United States Patent
Demarest et al.

(10) Patent No.: US 6,800,231 B2
(45) Date of Patent: *Oct. 5, 2004

(54) METHOD FOR CUTTING SUTURE

(75) Inventors: David D. Demarest, Parsippany, NJ (US); John F. Blanch, Tinton Falls, NJ (US); William F. Smith, Ringoes, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/776,658

(22) Filed: Feb. 5, 2001

(65) Prior Publication Data

US 2001/0007216 A1 Jul. 12, 2001

Related U.S. Application Data

(60) Division of application No. 08/804,478, filed on Feb. 21, 1997, now Pat. No. 6,206,677, which is a continuation-in-part of application No. 08/181,595, filed on Jan. 13, 1994, now abandoned.

(51) Int. Cl.⁷ .......................... B26D 7/02; B21D 39/00
(52) U.S. Cl. .......................... 264/138; 264/345; 83/14; 83/18; 83/23; 83/100; 83/240; 83/277; 83/451; 83/950
(58) Field of Search .............................. 83/15, 16, 153, 83/170, 277, 466, 907, 950, 14, 18, 23, 100, 240, 451, 175; 29/564.6, 516, 517, 243.157; 163/1, 5; 226/4, 104, 106, 108, 162, 167, 92; 606/224, 225, 226, 227; 264/138, 234, 345, 346; 425/143, 289

(56) References Cited

U.S. PATENT DOCUMENTS

| | | | |
|---|---|---|---|
| 284,496 A | 9/1883 | Seymour | |
| 2,236,833 A | 4/1941 | Pell et al. | |
| 3,183,743 A | 5/1965 | O'Donnell et al. | ........... 408/30 |
| 3,472,108 A | 10/1969 | Vandersip | |
| 3,611,551 A | 10/1971 | Shave et al. | |
| 3,811,244 A | 5/1974 | Killen et al. | |
| 3,857,313 A | 12/1974 | Endo | |
| 3,972,214 A | 8/1976 | Jagersberger | |
| 3,980,177 A | 9/1976 | McGregor | |
| 4,055,100 A | 10/1977 | Borzym | ........................ 83/454 |
| 4,072,041 A | * | 2/1978 | Hoffman et al. ................ 163/1 |
| 4,318,762 A | 3/1982 | Meyer | |
| 4,358,976 A | 11/1982 | Alviti | |
| 4,565,311 A | 1/1986 | Pugliese et al. ............... 225/94 |
| 4,672,871 A | 6/1987 | Gudmestad | |
| 4,722,384 A | 2/1988 | Matsutani | |
| 4,806,737 A | 2/1989 | Coates | |
| 4,832,025 A | 5/1989 | Coates | |
| 4,922,904 A | 5/1990 | Uetake et al. | |
| 4,942,796 A | 7/1990 | Dom et al. | |
| 5,156,788 A | 10/1992 | Chesterfield et al. | |
| 5,226,336 A | 7/1993 | Coates | |
| 5,438,746 A | 8/1995 | Demarest et al. | |
| 5,452,636 A | 9/1995 | Rattan | |
| 5,473,810 A | 12/1995 | Demarest et al. | |
| 5,477,609 A | 12/1995 | Demarest et al. | |
| 5,485,668 A | 1/1996 | Demarest et al. | |
| 5,487,216 A | 1/1996 | Demarest et al. | |
| 5,726,422 A | 3/1998 | Haase et al. ................. 219/388 |
| 6,058,821 A | 5/2000 | Demarest et al. ............. 83/385 |
| 6,128,816 A | * | 10/2000 | Demarest et al. .......... 29/564.6 |

FOREIGN PATENT DOCUMENTS

| | | | |
|---|---|---|---|
| EP | 0 428 253 | * | 5/1991 |
| FR | 2400984 | | 4/1979 |

* cited by examiner

*Primary Examiner*—Clark F. Dexter

(57) ABSTRACT

A method for cuffing suture, including: feeding the suture to a drawing axis for drawing and cutting thereof; heating the suture to stiffen a small length; gripping the suture and alternately drawing it along the drawing axis by first and second grippers; cutting the suture to provide uniform lengths; and providing a predetermined length of suture travel between the heating step and the cutting step, which is a discrete number, two or more, times the uniform length of suture being cut by the apparatus, to provide a discrete number, two or more, of apparatus cutting cycles between heating of the suture and cutting of the suture, whereby after heating of a small length of suture, the suture is cooled to allow setting and hardening of the suture material prior to cutting.

19 Claims, 15 Drawing Sheets

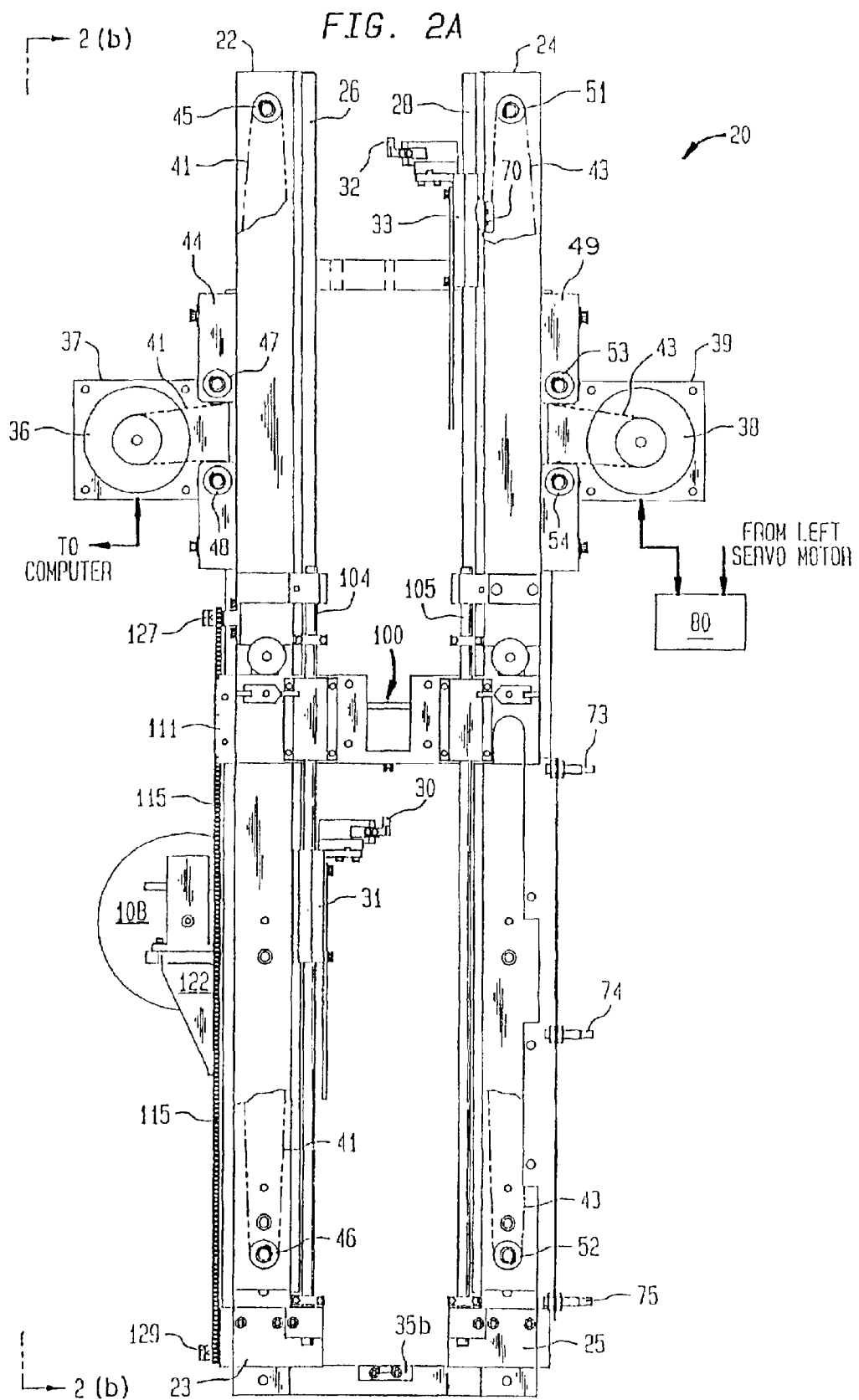

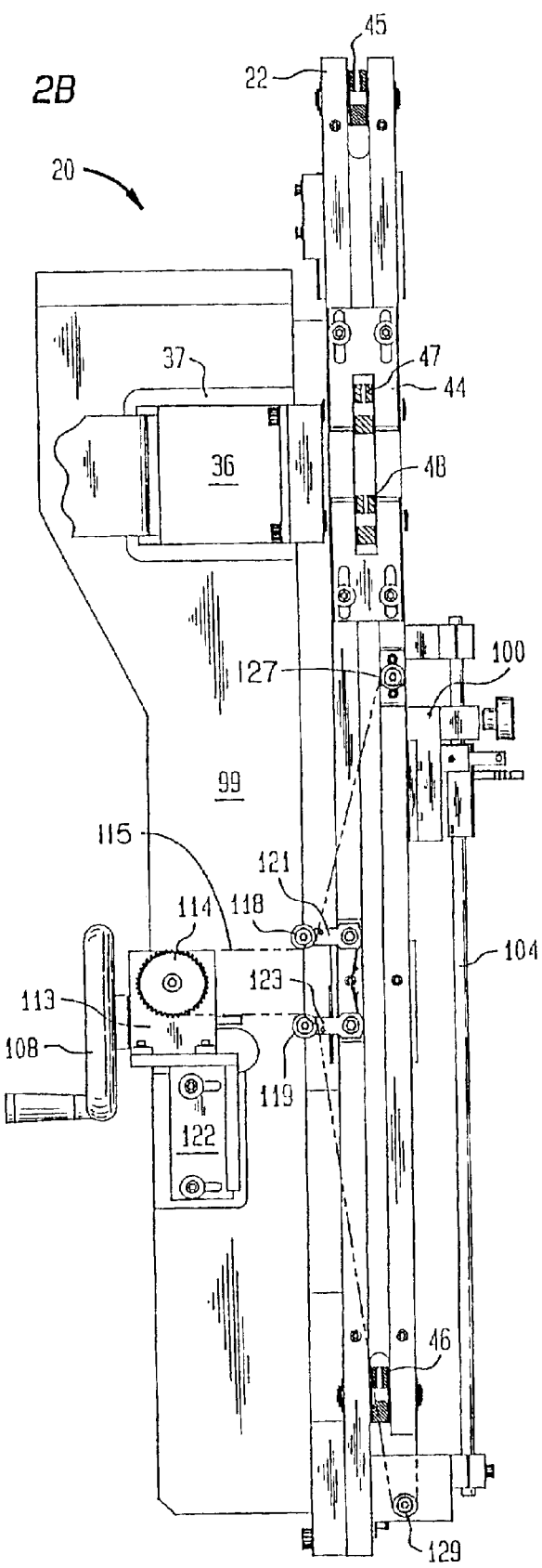

METHOD FOR CUTTING SUTURE

CROSS REFERENCE TO RELATED APPLICATION

The present application is a divisional of application Ser. No. 08/804,478 filed Feb. 21, 1997, now U.S. Pat. No. 6,206,677, which is a CIP of Ser. No. 08/181,595 filed Jan. 13, 1994, now abandoned.

BACKGROUND OF THE INVENTION

1. Field of the Invention

The present invention relates generally to an apparatus for cutting predetermined lengths of a flexible material such as thread, rope, wire, tubing, and the like, and more specifically, to an apparatus for automatically cutting a predetermined length of suture material for attachment to a surgical needle. More particularly, the present invention relates to apparatus for cutting an indefinite length of suture to different discrete lengths for subsequent swaging to surgical needles, and having a tipping assembly. The tipping assembly heats a predetermined small length of the suture to stiffen it in preparation for cutting the stiffened suture at a cutting assembly and inserting a stiffened lead cut end of the suture into an end of a needle for swaging thereto. A long length of suture travel is provided between the tipping assembly and the cutter assembly which is a discrete number of apparatus cutting cycles between the tipping and cutting operations to allow the tipped suture to cool prior to cutting.

2. Description of the Prior Art

The medical products industry presently utilizes semi-automated procedures for swaging sutures to surgical needles. For instance, as described in U.S. Pat. No. 3,611,551, manual intervention is required by an operator to accurately position a suture within the needle for swaging and to adjust swaging dies to increase or decrease swage pressure when suture strands of different gauges are to be swaged. This process is costly in terms of man-hour labor and efficiency because manual positioning is required for swaging to take place.

Presently, suture material may be supplied wound on a bobbin, or, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to change the rack each time a different length of suture is desired.

In U.S. Pat. No. 4,922,904, the suture material is supplied wound on a bobbin and is fed through various guide means and a heater for straightening the material, prior to insertion within the crimping cavity of the surgical needle. In one embodiment shown therein, an elaborate television monitoring means is required for aligning the drawn suture within the crimping cavity of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly is additionally fed a predetermined distance prior to cutting to obtain a suture strand of predetermined length. Thus, to obtain uniform lengths of suture material every time requires careful manipulations and precise controls, and the processes used to accomplish these tasks are also costly in terms of man-hour labor and efficiency.

It would be far more desirable to provide a suture cutting system and apparatus that is fully automated and which can automatically cut uniform lengths of suture material at high-speeds.

It would also be highly desirable to provide a suture cutting system that can accurately position suture material within the confines of the crimping ends of surgical needles at an appreciable rate and without elaborate techniques or manual procedures.

It would also be desirable to provide a suture cutting system which is operable under the control of a control system computer, and which can provide automatic adjustments to the swage tooling dies when different size sutures are swaged into various sized surgical needles.

SUMMARY OF THE INVENTION

Accordingly, it is an object of the instant invention to provide an automatic suture cutting assembly that virtually eliminates operator exposure to repetitive manual operations.

Another object of the instant invention is to provide a suture cutting apparatus that is fully automated and which can automatically and cleanly cut uniform lengths of suture material at high-speeds and without brooming of the suture tip.

It is another object of the instant invention to provide a suture cutting apparatus that includes a heat treating (tipping) device for stiffening a portion of the suture strand to be cut to aid in its insertion within a suture receiving end of a surgical needle.

Still another object of the instant invention is to provide a cutting apparatus which can be automatically set up to cut predetermined lengths of flexible articles or strands.

Yet another object of the present invention is to provide a suture cutting system that can accurately position suture material within the confines of a suture receiving opening of a surgical needle at an appreciable rate and without manual intervention.

These and other objects of the present invention are attained with an apparatus for cutting an indefinite length suture strand to uniform lengths for subsequent threading and swaging to a surgical needle having a suture receiving opening formed therein, wherein the apparatus comprises a drawing frame having at least one longitudinal member and defining a drawing axis parallel thereto. A means for feeding the indefinite length suture strand to the drawing axis for drawing and cutting thereof is provided. First and second gripping means are provided for gripping the indefinite length suture strand and drawing it along the drawing axis; the first gripping means being mounted for reciprocal movement on the longitudinal member. Also provided is a retractable cutting means for cutting the indefinite length suture strand to obtain a clean and broom-free horizontal cut. The second gripping means reciprocates to a start position along the drawing axis while the first gripping means is drawing the indefinite length suture strand to a predetermined distance beyond the retractable cutting means. The indefinite length suture strand is then inserted within the suture receiving opening of the needle and cut to a predetermined length by the retractable cutting means after the second gripping means has gripped the indefinite length suture strand at the start position.

Another object of the present invention is to provide an apparatus for cutting an indefinite length of suture to different lengths for subsequent swaging to surgical needles, and having a tipping assembly. The tipping assembly heats a predetermined small length of the suture to stiffen it in preparation for cutting the stiffened suture at a cutting assembly and inserting a stiffened lead cut end of the suture into an end of a needle for swaging thereto. A long length of suture travel is provided between the tipping assembly and the cutter assembly which is a discrete number of apparatus cutting cycles between the tipping and cutting operations to allow the tipped suture to cool prior to cutting.

In accordance with a preferred embodiment, the present invention provides an apparatus for cutting an indefinite length of suture to uniform lengths for subsequent threading and swaging to surgical needles having a suture receiving opening formed therein. The apparatus comprises a drawing frame, having at least one longitudinal member and defining a drawing axis parallel thereto. A tipping assembly is provided for heating a predetermined small length of the suture to stiffen the small length of suture after subsequent cooling thereof, in preparation for cutting the suture at the stiffened small length and inserting a stiffened lead cut end of the suture into an end of a needle for swaging thereto. First and second grippers are provided for gripping the indefinite length suture and alternately drawing it along the drawing axis. The first and second grippers are mounted for reciprocal movement on the longitudinal member(s). In operation one of the first and second grippers draws the indefinite length suture to a position beyond a cutter assembly, while the other of the first and second grippers reciprocates to a start position along the drawing axis before the cutting, assembly, such that the first and second grippers are used alternately to draw suture through the apparatus and feed the suture into a needle. The cutting assembly severs the indefinite length suture to provide uniform lengths of suture. In accordance with the present invention, a predetermined long length of suture travel is provided between the tipping assembly and the cutter assembly, wherein the predetermined long length of suture travel is a discrete number, two or more, times the uniform length of suture being cut by the apparatus. This provides a discrete number, two or more, of apparatus cutting cycles between tipping of the suture at the tipping assembly and cutting of the suture at the cutting assembly, such that after heating of a small length of suture at the tipping assembly, the suture is cooled to allow setting and hardening of the suture material prior to cutting.

In greater detail, the discrete number of uniform length of suture or apparatus cutting cycles comprises at least three. At least one small diameter idler roller is provided for guiding the suture to the tipping assembly, and after heating thereat, the suture is drawn to and rotates around a large diameter idler roller. The larger diameter of the idler roller is provided because the small length of suture which has been heated at the tipping assembly has begun to harden and set by the time the heated suture reaches the large diameter idler roller. The large diameter thereof facilitates the suture to travel therearound and change direction without picking up a permanent curved set from the large idler roller, to provide a straight suture, without any curve, when it is subsequently cut and inserted into a needle. The large diameter idler roller has a diameter larger than 6 inches, and in one embodiment is 7 inches. The tipping assembly is positioned near the top of the apparatus, and the large diameter idler roller is positioned near the bottom of the apparatus, and the suture reverses direction at the large diameter roller and is drawn vertically upwardly to the first and second grippers and the cutter assembly.

The position of the cutting assembly along the drawing axis is continuously adjustable to provide an infinite number of possible different lengths of cut suture. For each different position of the cutting assembly, the tipping assembly is adjustably positioned at a different predetermined position in the apparatus to provide for the tipped section of suture to be precisely positioned at the cutter assembly after a discrete number of apparatus cycles. The tipping assembly includes a pointer positioned adjacent to a linear measurement scale stationarily positioned in the apparatus, such that the position of the tipping assembly is precisely controlled by aligning the pointer with a specified reading on the linear measurement scale. The position of the tipping assembly in the apparatus is adjustable by rotation of a handcrank and precision leadscrew.

The suture is initially drawn into the apparatus, and extends to and is wrapped around a tension roller which is mounted on one end of a torque motor, which applies a given tension to the suture as it is pulled through the apparatus by the first and second grippers. The suture is wrapped around the tension roller a multiple number of times, in one embodiment twice. Each different suture size and material has a different tension applied thereto by the torque motor as it is drawn through the apparatus, and the specific tension force is downloaded from a computer program at each suture batch changeover. Moreover, each of the first and second grippers includes a releasable suture clamp positioned thereon which releasably clamps the suture during an initial auto threading of a new lead of suture through the apparatus.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 2(a) is a detailed view of the cutting assembly tower of the instant invention.

FIG. 2(b) is a detailed side view of the cutting assembly taken along line 2(b)—2(b) of FIG. 2(a) showing the pulley assembly for moving tip and cut assembly 100 of the instant invention.

DETAILED DESCRIPTION OF THE PREFERRED EMBODIMENT

Figure 1:
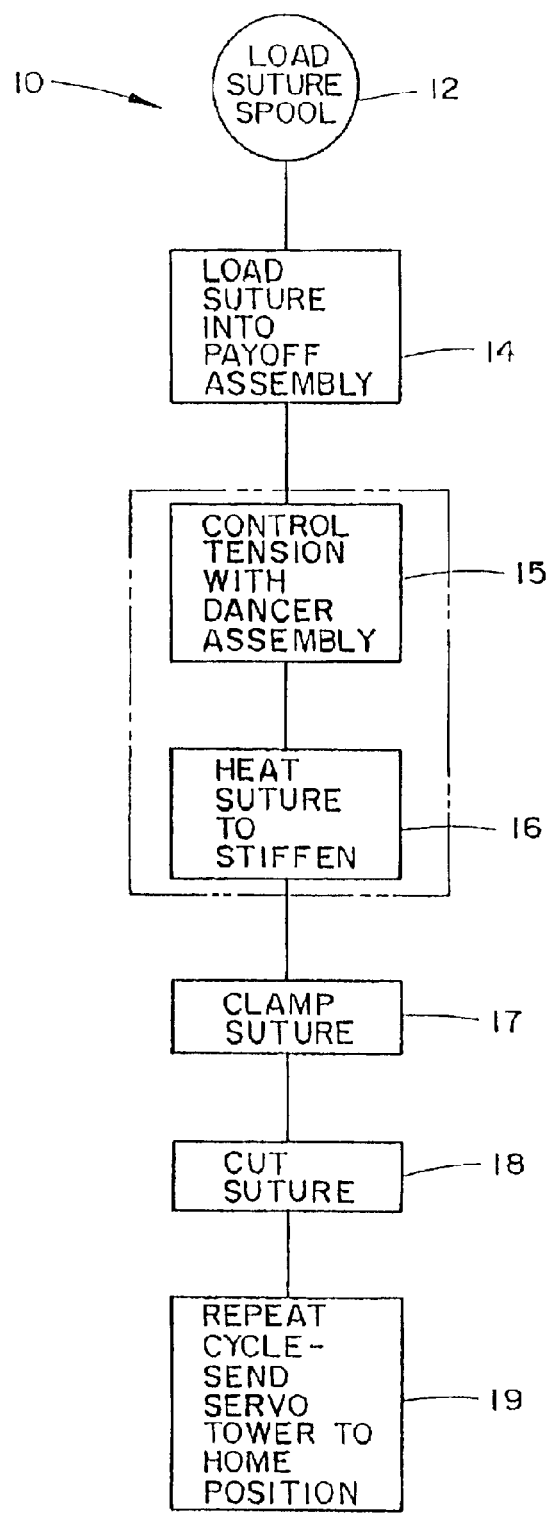
FIG. 1 is a block diagram showing the process used in the instant invention for cutting a length of material.

FIG. 1 is a block diagram generally illustrating the process 10 used to feed and cut predetermined uniform lengths of material. It should be understood that flexible materials such as thread, tubing, rope or wire of any gauge may be cut using the apparatus of the instant invention. The preferred embodiment of the instant invention is intended for use in cutting uniform lengths of suture material to enable automatic swaging of the cut suture to a surgical needle. A more detailed description of the needle threading and swaging system and the swaging station itself can be found in U.S. Pat. No. 5,438,746 and U.S. Pat. No. 5,477,609, assigned to the same assignee of the present invention. For descriptive purposes, the preferred embodiment discussed below is intended for cutting suture material used by medical personnel in hospitals and doctors' offices.

Generally, in the automatic cutting process 10 shown in FIG. 1, the suture material is supplied in various spools and configurations that may carry up to 5000 yards of material. This is indicated as step 12 in FIG. 1. Next, at step 14, the suture material is loaded into a payoff assembly which is part of a drawing tower apparatus to be described in detail below. This payoff assembly feeds the suture material from the spool to enable cutting thereof. When larger spools of material are used, the material may be optionally loaded in a driven spool feed assembly with a dancer as indicated at step 15 to ensure that the material does not break or snap when in tension.

Some material used in this apparatus may require extra treatment or processing. For instance, as described in detail below, it may be desirable to heat the suture material under tension at the suture tip in order to stiffen the material to facilitate the positioning thereof within the suture receiving opening of a surgical needle. Thus, at optional step 16, heat may be applied at specific points along the length of suture material. At step 17 of the block diagram of FIG. 1, the suture material is held by a bottom movable gripper located at a lower portion of the drawing tower to maintain control of the indefinite length strand of material after the suture material above it is cut off as indicated at step 18. In the subsequent cycle, this lower gripper reciprocates to an upper position of the drawing tower while drawing the suture material, while the top gripper descends, and the cycle is repeated as indicated as step 19 in FIG. 1. The process of advancing suture material 55 by alternating grippers at each cycle eliminates the recycle or return time for returning the gripper to the original position. This makes faster machine speeds and hence, higher production rates possible. A detailed explanation of the apparatus used to carry out each step will be explained in further detail hereinbelow.

Figure 5:
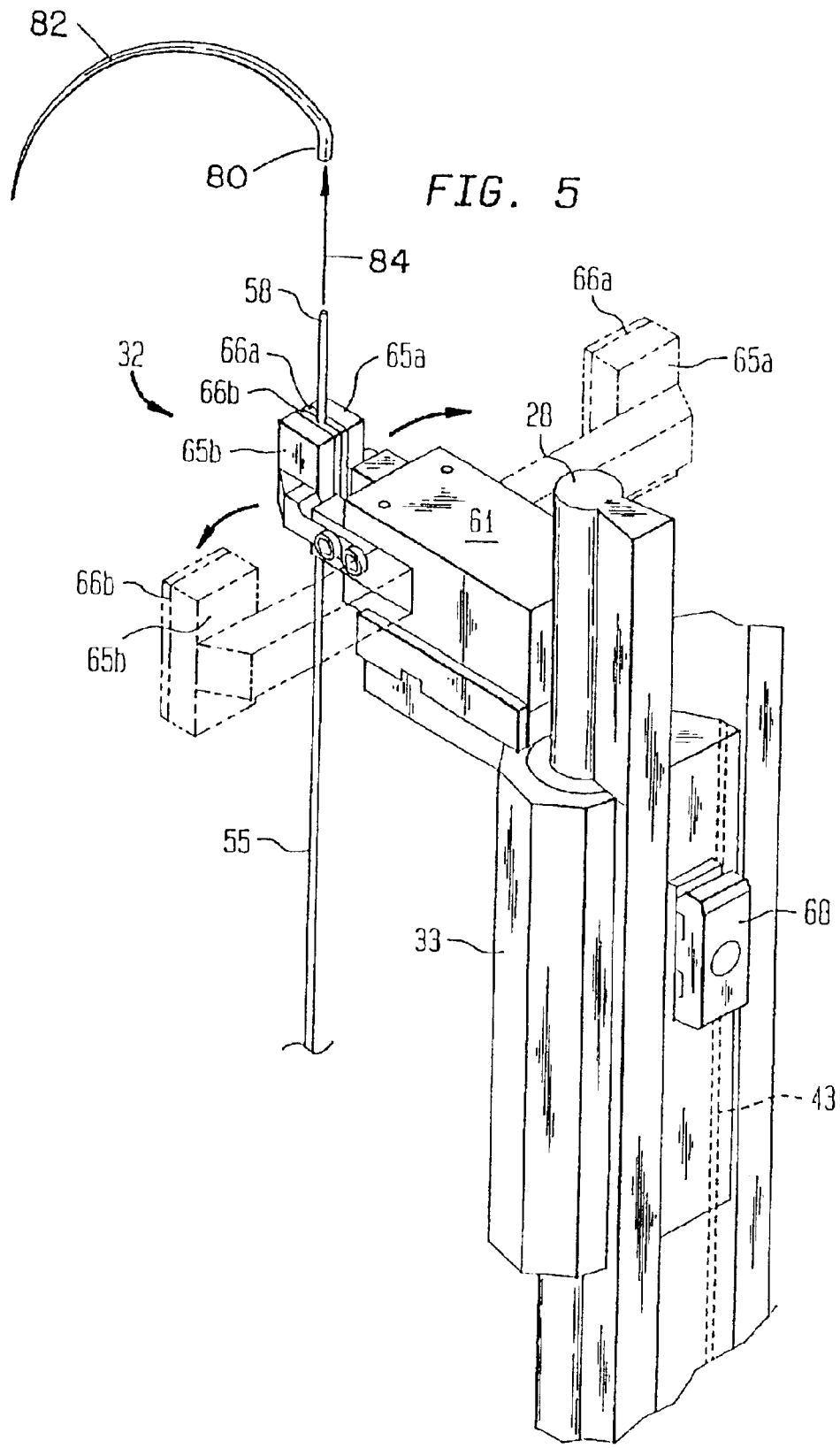
FIG. 5 is an enlarged view of a gripper assembly having gripper arms shown in their closed (suture gripping) and open positions.

The first step of the automatic cutting process 10 involves feeding the indefinite length suture material at one end of the payoff assembly. In the preferred embodiment, the payoff assembly is embodied as a drawing tower 20 shown in FIG. 2(a). The drawing tower 20 comprises left side rail 22 mounted on suitable left mounting block 23 and right side rail 24 mounted on suitable right mounting block 25 and defining a drawing frame for drawing an indefinite length of suture material along a drawing axis therebetween. Located parallel to the left and right side rails 22,24 and suitably connected thereto are respective left guide rod 26 and right guide rod 28. The first gripper means or right gripper 32 reciprocates up and down along right guide rod 28 while the second gripper means or left gripper 30 reciprocates up and down the left guide rod 26. Each of the grippers 30,32, as will be explained below, grip the suture material that is drawn from a spool through pulley 35b located at the bottom of the drawing tower 20, and carries the material to the upper end of the tower. The right gripper 32 is mounted on right gripper carrier 33 for vertical movement along right guide rod 28, and the left gripper 30 is mounted on left gripper carrier 31 for vertical movement along left guide rod 26 as shown in FIG. 2(a). FIG. 5 illustrates a gripper 32 (similar to 31) having a gripper arm drive 61 that is pneumatically operated to drive a pair of retractable gripper arms 65a, 65b toward each other to a suture gripping position, or, away from each other to an open position. Each retractable gripper arm is provided with a non-metallic pad 66a, 66b for gripping the tipped end 58 of the suture material 55 at an end thereof when actuated to the gripping position. To release the grip of the suture, gripper arms 65a,65b are retracted approximately 180 degrees apart in the direction indicated by the arrows of FIG. 5 to the open position. When in the open position the gripper arms 65a, 65b do not interfere with the motion of the other vertically moving gripper as it reciprocates along the respective left or right rod carrying the next strand of suture material, nor will it interfere with the cutter assembly 200 as will be explained below. The retractable nature of the grippers and of the cutting assembly (discussed hereinbelow) enables single drawing axis operation.

As mentioned above, each gripper carrier and gripper thereof is designed to advance vertically along the respective left and right rods. As shown in FIG. 2(a), the right gripper 32 and gripper carrier 33 are driven by right servo motor 38 which is mounted to the right side rail 24 by right motor mounting bracket 39. Similarly, the left gripper 30 and gripper carrier 31 are driven by left servo motor 36 which is mounted to the left side rail 22 by left motor mounting bracket 37. In the preferred embodiment, both left and right servo motors are interfaced with and controlled by a control system computer, indicated generally as numeral 80 in FIG. 2(a), and as explained in further detail in U.S. Pat. No. 5,487,216, assigned to the same assignee of the present invention. As shown in FIG. 2(a), right servo motor 38 drives timing belt 43 which consequently enables vertical positioning of right gripper carrier 33 along right rod 28, while the left servo motor 36 drives timing belt 41 which consequently enables vertical positioning of left gripper carrier 31 along left rod 26. As FIG. 5 illustrates, timing belt 43 is clamped to its respective gripper carrier 33 by a timing belt clamp 68 located on the back of the gripper carrier. A similar timing belt clamp (not shown) is provided on gripper carrier 31 for clamping timing belt 41 to enable vertical movement of gripper 30. FIG. 2(a) shows timing belt 41 engaging upper left pulley 45 and lower left pulley 46 as well as idler pulleys 47,48 which are part of tensioner block 44 that adjusts the tension of the timing belt 41 and consequently of left gripper carrier 31. Likewise, FIG. 2(a) shows timing belt 43 engaging upper right pulley 51 and lower right pulley 52 as well as idler pulleys 53,54 which are part of tensioner block 49 that adjusts the tension of the timing belt 43 and consequently of right gripper carrier 33.

Figure 3:
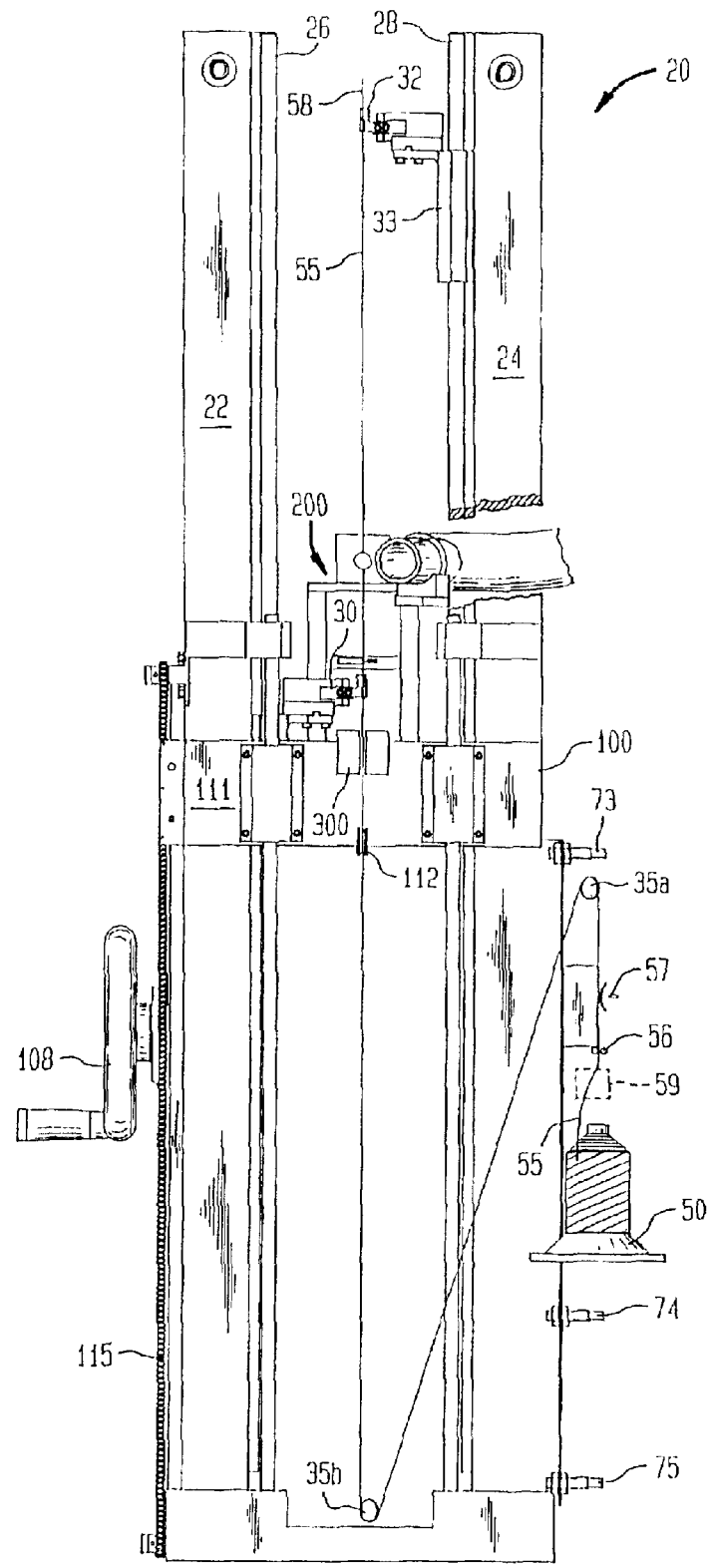
FIG. 3 is a detailed view of the servo tower 20 illustrating cutter assembly 200 mounted on tip and cut carrier 100, and the king spool supplying the suture strand.

FIG. 3 shows suture material 55 being pulled by right gripper 32 from a king spool 50. In an alternative embodiment, the spool may be motor driven in which case a dancer assembly 59 may be provided to control the tension of the material as it is being fed. To feed the indefinite length suture material to the drawing tower, the suture material 55 is first threaded through eyelet 56 to an optional knot detector 57 which senses any sudden change in the thickness of the suture material. Detection of a knot in material 55 will trigger the control system 80 to discard the cut strand of material at a subsequent operation. The suture material 55 is then advanced through the knot detector, over pulleys 35a and 35b located at the bottom of the drawing tower 20, and around pulley 112 which is mounted on the lower portion of tip and cut carrier 100 that is illustrated near the center of the tower in FIG. 3. As will be explained in detail below, and as illustrated in FIG. 3, the right gripper 32 is gripping the suture material 55 at a tipped portion of the free end 58.

Figure 4:
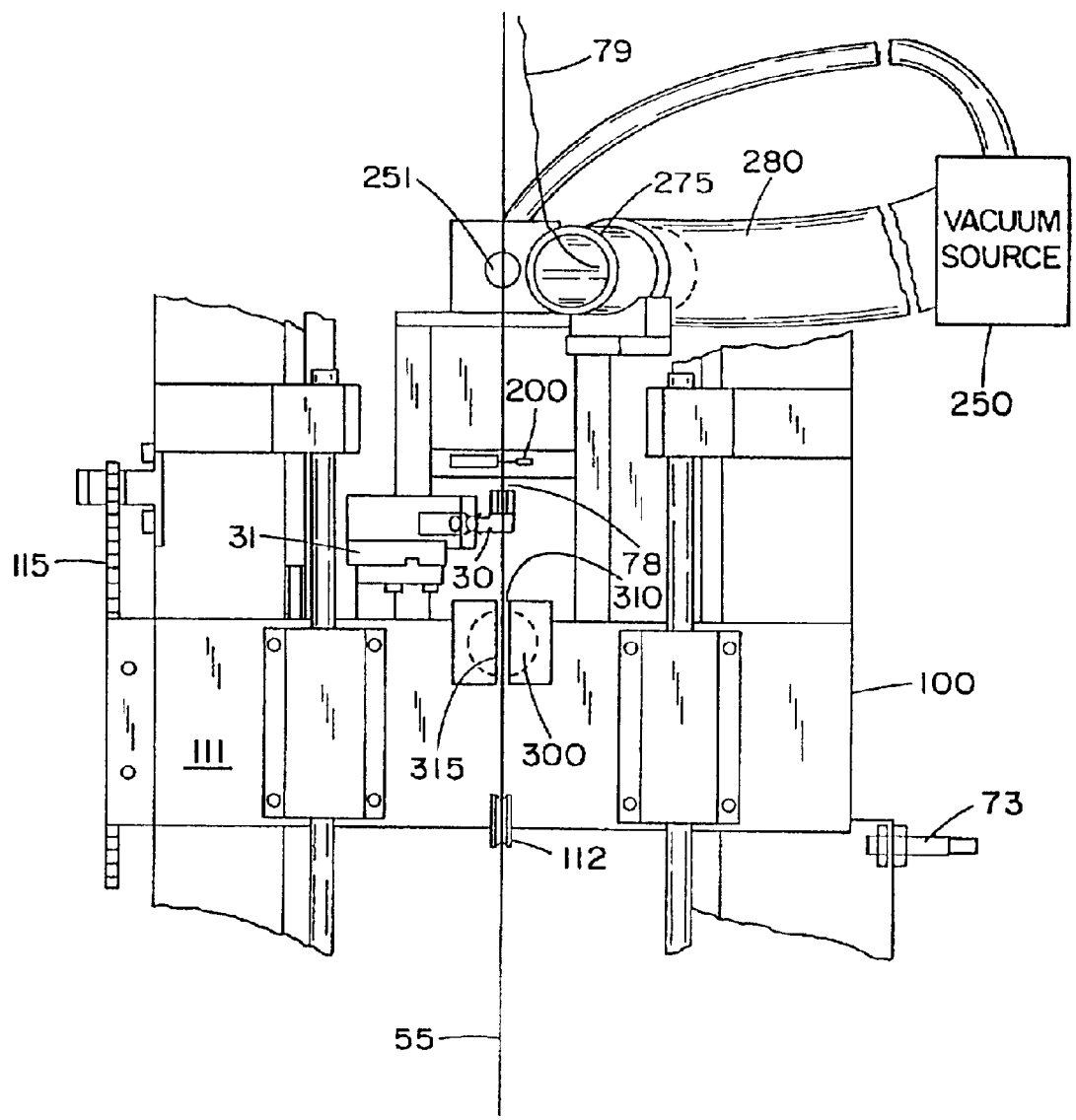
FIG. 4 is a detailed view of the tip and cut carrier 100 of the instant invention illustrating vacuum assembly and tipping assembly 300 mounted thereon.
Figure 6:
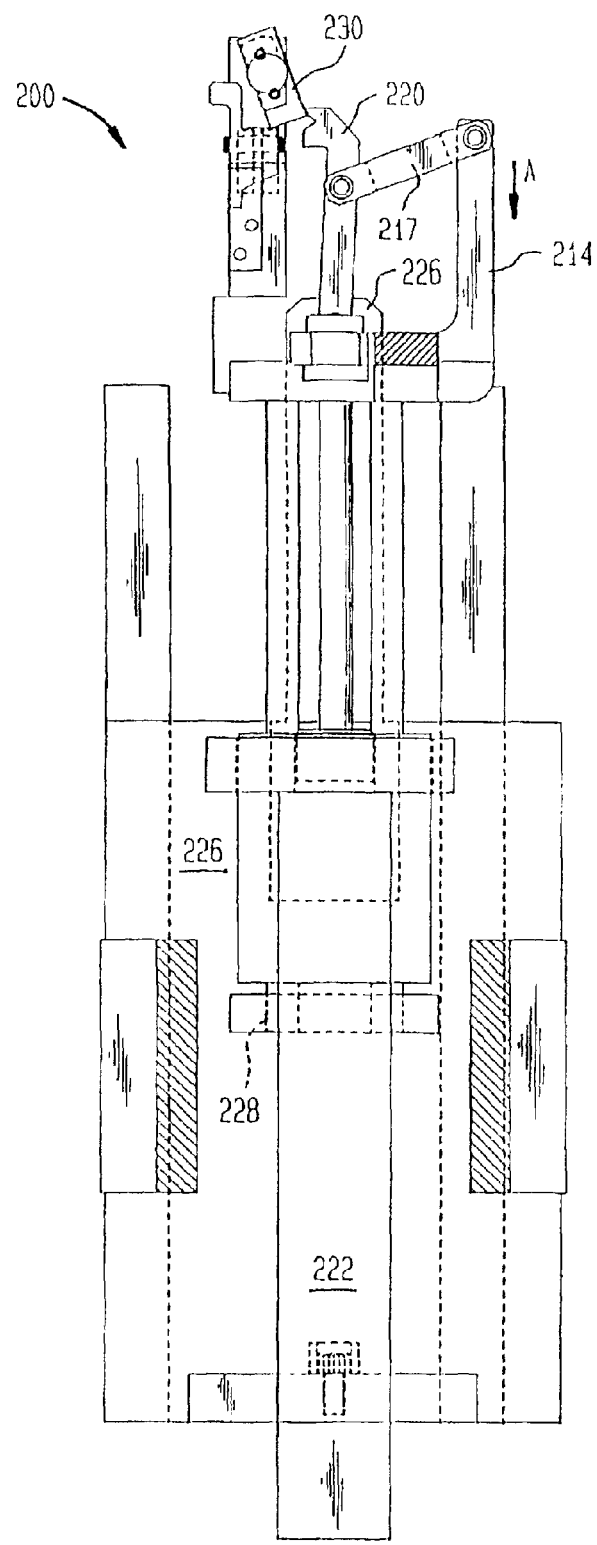
FIG. 6 is a detailed top view of the cutter assembly 200 for cutting material in the instant invention.
Figure 7:
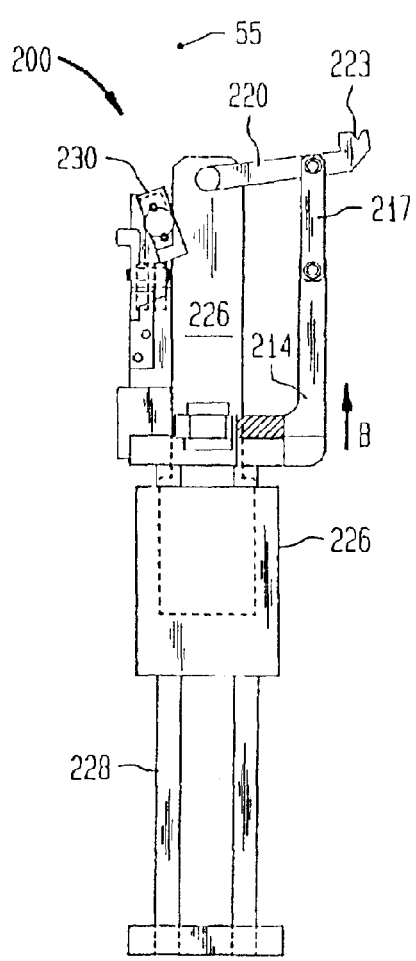
FIG. 7 is a detailed top view of the cutter assembly 200 shown in a fully retracted position.
Figure 8:
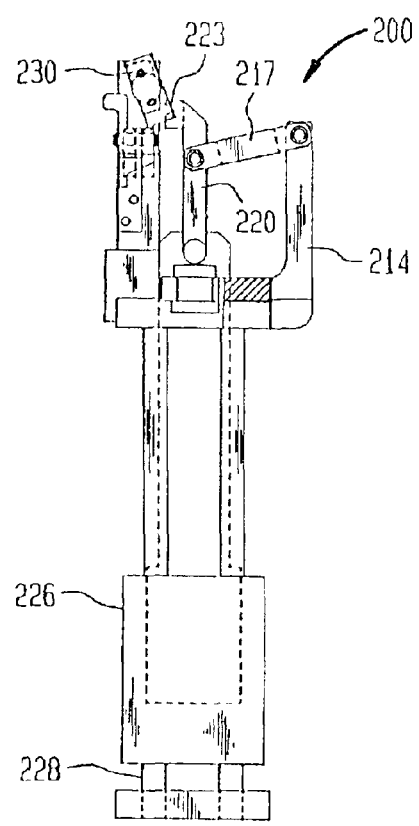
FIG. 8 is a detailed top view of the cutter assembly 200 shown in a fully extended (cutting) position.

As shown generally in FIGS. 3 and 4, tip and cut carrier 100 provides the support for tipping assembly 300 that applies heat to a specific location of the suture material, and also provides support for the cutter assembly 200 that cuts the suture material, as discussed in further detail with respect to FIGS. 6–8. FIG. 2(a) shows the tip and cut carrier 100 positioned along shafts 104 and 105 which are located parallel to respective left and right rods 26,28. In the preferred embodiment, vertical movement of the tip and cut carrier 100 is accomplished by cranking handwheel 108 shown in FIG. 2(b). Other embodiments may implement a computer controlled servo motor to vertically register the tip and cut carrier 100 prior to cutting the material. In the operation of the apparatus, both the stroke of the grippers 30,32 and the positioning of the tip and cut carrier 100 along drawing tower 20 dictates the length of the material that will be cut.

As illustrated in FIG. 2(b), cranking handwheel 108 actuates a gearbox 113 that rotates chain drive sprocket 114. The gearbox 113 is mounted on a gearbox mounting bracket 122 which, in turn, is mounted to frame member 99. A cable chain 115 is engaged with chain drive sprocket 114 to actuate movement of the tip and cut carrier 100 as shown in FIG. 2(b). The cable chain 115 also engages chain idler sprockets 118 and 119 which are rotatably mounted to upper tensioner pulley bracket 121 and lower tensioner pulley bracket 123, respectively. The vertical positioning of tensioner pulley brackets 121,123 may be adjusted to vary the slack in cable chain 115. Cable chain 115 also engages chain idler sprockets 127 and 129 which are suitably mounted on left side rail 22. As shown in FIG. 3, the back 111 of tip and cut carrier 100 is clamped to cable chain 115.

As previously mentioned, tip and cut carrier 100 includes guide pulley 112 that positions the suture material 55. The suture material is received under tension from guide pulleys 35a, 35b. As can be seen in FIG. 3, the lower threading pulley 35b, guide pulley 112, left gripper 30 and right gripper 32 are vertically aligned so that the cutter assembly 200 will always cut horizontally across the strand of material as will be explained below.

FIGS. 6–8 illustrate in detail the cutter assembly 200 which is suitably mounted to the tip and cut assembly 100 as shown in FIG. 4. As shown in FIG. 7, the cutter assembly comprises overcenter linkage 214 having a link arm 217 pivotally connected at one end thereof. A pivotal locator arm 220 is fixedly connected to link arm 217 at a second end thereof and is illustrated in FIG. 7 as substantially transverse thereto. The other end of locator arm 220 is pivotally connected to a stationary guide mechanism 226. Note, that all linkages described herein are simple pin linkages, the actuation of which creates the dwell moment for cutting the suture strand and obviates the need for complicated cams, slots, and sliding mechanisms.

As shown in FIG. 7, the stationary guide 226 is located in a plane perpendicular to the drawing axis of the suspended strand of material 55, and is located a distance from the strand approximately equivalent to the length of locator arm 220. In addition, overcenter linkage 214, locator arm 220, and cutting blade 230 all lie in planes perpendicular to the drawing axis of the strand of material 55.

A retractable ball slide 228 is mounted on the stationary guide 226 and coupled to overcenter linkage 214 for moving the overcenter linkage 214 and blade 230 along the stationary guide 226 in the direction indicated by arrow "A" in FIG. 6 from a cutting position to a retracted position shown in FIG. 7. As the ball slide 228 is actuated to move overcenter linkage 214 to a retracted position, the locator arm 220 is pivoted away from the strand 55 and the blade 230 is retracted. Thus, when the cutter assembly 200 is in the retracted position prior to cutting of the strand and immediately thereafter, the blade 230 and locator arm 220 do not interfere with the reciprocating motion of the grippers 30,32 along the drawing tower 20, nor do they come in contact with the suspended strand 55. In the preferred embodiment, pneumatic air cylinder 222 enables reciprocating movement of the ball slide 228 along stationary guide 226 as shown in FIG. 6.

When cutting the strand of material 55, the retractable ball slide 228 reciprocates in the direction toward the strand 55 indicated by arrow "B" in FIG. 7 to bring the overcenter linkage 214, and consequently the cutting blade 230 and locator arm 220 to the cutting position shown in FIG. 8. As the overcenter linkage 214 moves to the cutting position, the link arm 217 translates the movement of the ball slide 228 into pivotal movement of the locator arm 220. Locator arm 220 is provided with a V-shaped support block having a notch 223 which functions to engage the strand of material 55 to be cut as the arm is pivoted into the cutting position. The V-shaped notch also functions to support the strand on two sides of the strand 55 while it is being horizontally cut on a third side. This enables clean, broom-free cuts especially of multi-filament suture material, which tends to form a broom end when the strand is under tension and is cut by scissors, or, when the multi-filament strand is sliced and not properly supported.

The cutting blade 230 of cutter assembly 200 is fixedly mounted to reciprocating ball slide 228 at a slight angle relative thereto and in a plane parallel with that of the locator arm 220. In the preferred embodiment, a single action by the pneumatic air cylinder 222 will enable movement of the reciprocating ball slide 228 along stationary guide 226. This consequently enables pivoting of locator arm 220 from its retracted position (FIG. 7), so that V-shaped support notch 223 engages the strand 55 at two sides thereof while a third side of the strand bears upon the cutting edge of blade 230 as the blade moves towards the supported strand 55 traversing the drawing axis thereof. Thus, the strand 55 is cut in a dwell moment of the locator arm after the locator arm 220 has pivoted in the direction toward the blade 230 to the cutting position shown in FIG. 8. The blade 230 slices the strand of material while the strand is held stationary by locator arm 220 by virtue of the angled orientation of the blade with respect to the axis of reciprocation illustrated in FIGS. 7 and 8. In the preferred embodiment, the slice ratio is 1:1 or greater, with the blade 230 angled at approximately 45 degrees relative to the axis of reciprocation, so that the strand 55 is cut an amount equivalent to the distance the blade 230 traverses the drawing axis.

Preparing a predetermined length of (suture) material for cutting and swaging is accomplished as follows:

First, the indefinite length strand of suture material 55 is manually threaded through eyelet 56, and about pulleys 35a, 35b, and 112. The first gripping means including right gripper 32 is actuated to the gripping position as illustrated in FIG. 5, so that the suture strand 55 will be gripped in the manner described above. Next, the gripper draws the material strand 55 to the top portion of the drawing tower as shown in FIG. 3. Then, operable under the control of the control system computer 80, the right servo motor 38 is enabled to drive the lead (right) gripper vertically along right rod 28 to a predetermined height, all the while carrying suture material 55 in the manner described above. As shown in FIG. 2(a), proximity sensor 70 is mounted at a position along the right side rail 24 to verify that the right gripper 32 has reached its desired position. Likewise, a proximity sensor (not shown) is mounted at the desired height along the left side rail 22 to verify that the left gripper 30 has reached its desired location. As shown in FIG. 2(a), proximity sensors 73,74, and 75 are positioned vertically at different heights along the drawing tower 20 to additionally predetermine suture material lengths to be cut. Specifically, the locations of the proximity sensors 73,74, and 75 sense the positioning of the tip and cut assembly 100 as controlled by handcrank 108 in order to notify the control system 80 to change the reciprocating travel of grippers 30,32.

In the preferred embodiment shown in FIG. 3, the lead gripper (gripper 32) grips the suture material on the tipped portion slightly below its tipped end 58 to register the tipped end for positioning within the suture receiving opening 80 of a precisely registered surgical needle 82 in the direction of arrow 84 for swaging thereof (e.g., servomotor 38). To accomplish this, the lead gripper servomotor (e.g., servomotor 38) first advances the lead gripper for a long stroke distance, which may range from 12 inches to 36 inches depending upon the desired length of said suture strand, but is 16.1 inches in the preferred embodiment. The long stroke moves gripper 32 from a position at the tip and cut carrier 100 to the position illustrated in FIG. 3. Simultaneously therewith, the other servomotor, e.g., servomotor 36, positions the bottom gripper, e.g., left gripper 30, along left rod 26 at a location preferably below the position of the cutter assembly 200 as shown in FIGS. 3 and 4. It is understood that the lead gripper is gripping the material 55 at all times during the long stroke, while the bottom gripper is in its open position and not gripping.

The next step, indicated in FIG. 1 as step 17, is to position the lead gripper 32 so that the tipped end 58 of the suture material is positioned within the suture receiving opening of a surgical needle for swaging thereof. To accomplish this, the lead gripper 32 must again advance the suture material 55 for a short stroke distance of about 1.9 inches in the preferred embodiment, so that the tipped end 58 will advance precisely into the suture receiving opening of the surgical needle for a subsequent swaging operation to take place.

It should be understood that in another embodiment of the invention this step may consist of handing off the tip of the material to a subsequent material handling device, e.g., connecting a length of wire to a wire harness, or the like.

As the tipped end 58 of the indefinite length suture strand is advanced during the short stroke distance prior to swaging, a heated tipped portion 78 of the material 55 that has been heated by tipping assembly 300, (explained hereinbelow), advances to a position slightly above the location of the left gripper 30 and adjacent the cutter assembly 200. Then, while the automatic swaging of the tipped end 58 to the surgical needle takes place at the top of the tower 20, the left gripper 30 (lower gripper) is actuated to grip the material 55 in the tipped portion 78, i.e., the portion of the suture material heated by tipping assembly 300 as shown in FIG. 4. Simultaneous with the engagement of left gripper 30, the right (lead) gripper 32 is actuated to release its grip on the suture material.

Figure 9:
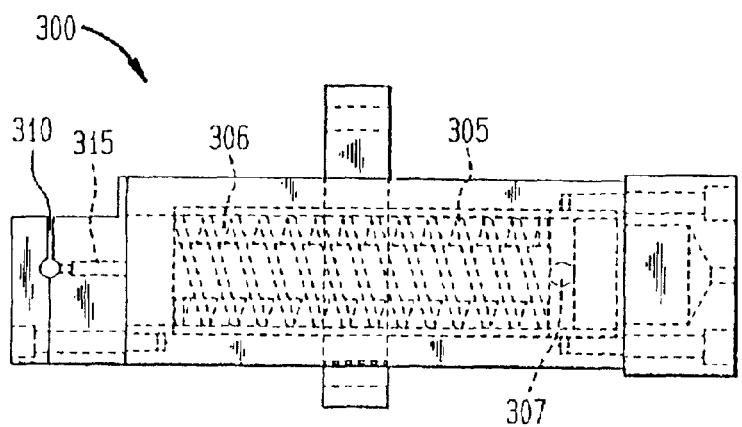
FIG. 9 is a detailed top view of the tipping assembly 300 for heating a portion of the suture material.

In the optional step indicated as step 16 in FIG. 1, the right or lead gripper is halted after the long stroke so that the portion of the suture material 55 may be heated (tipped) prior to cutting thereof. Heating the suture under tension and the subsequent cooling thereof will stiffen the material and aid in the positioning and subsequent swaging of the tip of the material within the confines of the suture receiving end of the surgical needle. The operation of the tipping assembly 300 will now be explained as follows:

As shown in FIG. 9, the tipping assembly 300 is essentially an oven comprising a heat exchanger unit 305 that heats the air in the heater cavity 306. When a pulse of incoming air is provided to the heat exchanger input 307, the heated air is displaced and it provides a pulse of heated air to a vertical cylindrical cavity 310 as shown in FIG. 4 and in the top view of FIG. 9. As shown in FIG. 4 the heated air is forced through horizontal orifice 315 for a predetermined duration so that the length of suture material 55 suspended in tension through vertical cavity 310 will be heated. The control system computer 80 controls the duration of the heat pulse so that the material is adequately heated and will have sufficient time to cool before the cutting operation. The temperature of the heated pulse may vary depending upon the surface area of the strand suspended through the vertical cavity 310. Preferably, the tipping assembly 300 is located at a position that is located slightly below the bottom or left gripper. As mentioned above, this is required so that when the suture material 55 is advanced the short stroke distance, the tipped portion 78 of material 55 will advance a corresponding distance so that it may be cut by cutter assembly 200. This ensures that the bottom gripper, e.g., left gripper 30, will grip the material having a new tipped end 58 for the next suture draw/insert cycle.

It should be understood that various other "tipping" technologies will work depending upon the type of suture material that is being processed. For instance, when VIC-RYL® and VICRYL®-like suture materials are used, tensioning of the strand, in addition to hot air application to a strand will enable the surface thereof to be stiffened and/or melted and recast to form a stiffened tip. The application of tension in addition to a heated, grooved, die for forming the tip diameter of VICRYL® suture materials may also be used; however, the use of a die to form the tip diameter, requires closer control of the strand location to ensure that a tip gets into the die groove for every cycle. For wax-impregnated suture materials like silk, the application of tension only at predetermined locations, will form a stiffened portion of the suture strand at those locations. Another tipping method for use with braided suture materials, involves applying and penetrating the braid with a dilute resin material such as General Electric's VITEL® having a high solvent content, and quick drying the applied portions with hot air while maintaining tension of the suture strand materials to form a stiffened tip thereof.

After swaging of the surgical needle takes place and the left gripper 30 has secured the suture strand, the suture material 55 is cut by the cutting assembly 200 in the manner described above and as indicated in step 18 in FIG. 1. In the preferred embodiment shown in FIG. 4, a vacuum air flow from vacuum source 250 is energized to pull the strand of material 55 toward the nylon screen 251 to more precisely locate the suture strand in the target zone of the cutter. After cutting of the indefinite length suture material 55 at the tipped portion 78, the tail end of the length of the cut suture material that had been swaged to the surgical needle is sucked into a large vacuum pipe 275, that is connected to a vacuum source 250 by vacuum hose 280 at shown in FIG. 4. The vacuum created in vacuum pipe 275 exerts a mild tension on the strand of material to keep the tail end 79 from entanglement or coming into contact with the machinery. However, it is mild enough to allow the strand to be pulled out of the pipe 275 as the armed needle and suture are handed off for further downstream processes.

FIG. 4 shows the left gripper 30 positioned slightly below the cutter assembly 200 so that the indefinite length strand will be gripped when the definite length swaged strand is cut. Thus, the left gripper now grips the suture material 55 having a tipped end 58 and it now becomes the lead gripper. The next cycle begins with the lead gripper vertically drawing the material 55 along the height of the drawing tower 20 for the long stroke to position the next strand to be cut for insertion within the surgical needle.

Figure 10:
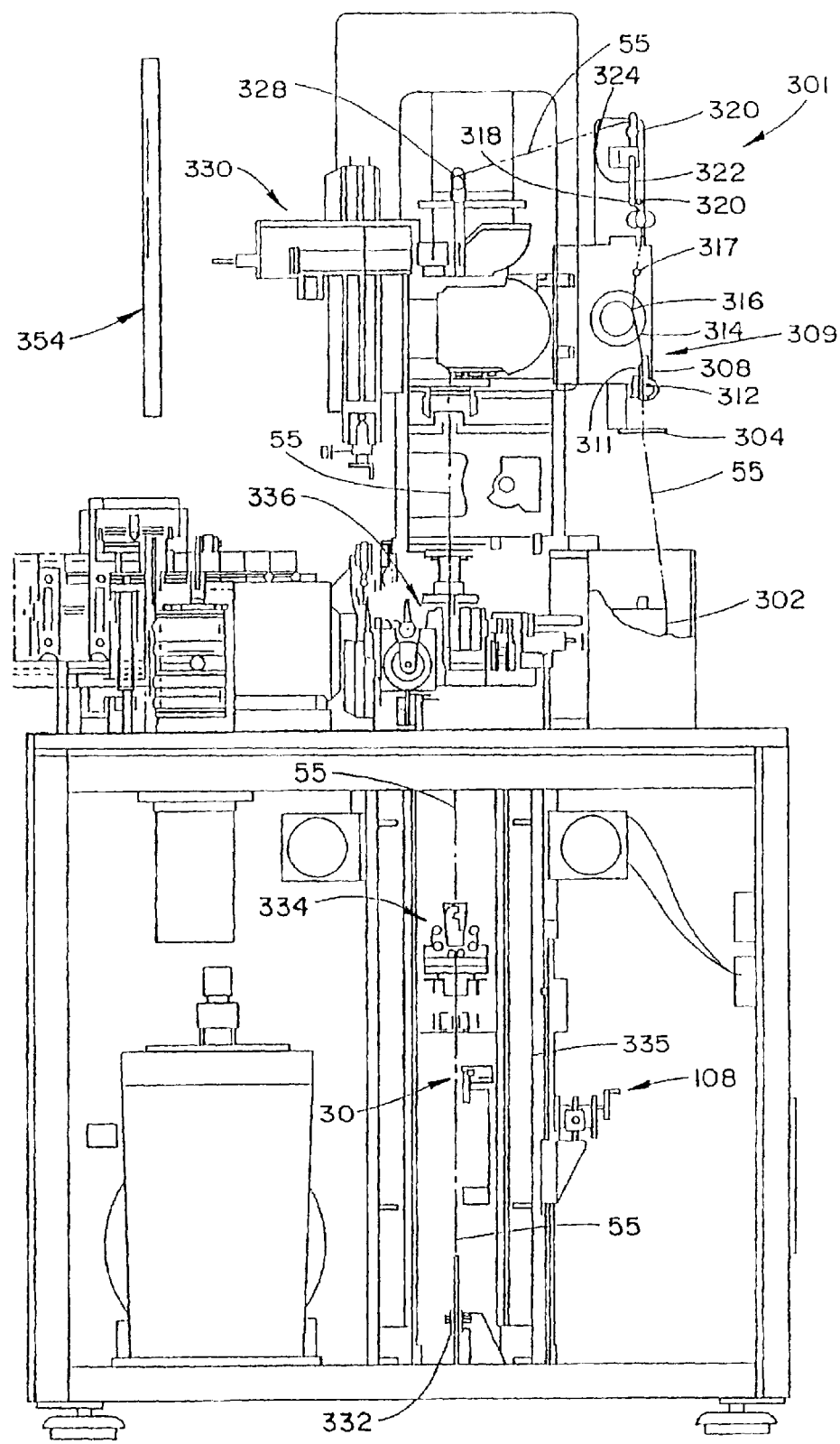
FIG. 10 illustrates a front elevational view of one designed embodiment of a servo tower, similar to that shown in FIGS. 2–5, and shows the suture path therethrough and the locations of the major assemblies thereof.

FIG. 10 illustrates a front elevational view of one designed embodiment of a servo tower 301, similar to that shown in FIGS. 2–5, and shows the suture path therethrough. Suture 55 is pulled off one end of a supply roll 302 mounted to one side of the servo tower, through the center of an annular guide disc 304, and into a mechanical tensioner 309. The mechanical tensioner can comprise a stationary guide frame 308 and a pivotally mounted guide frame 311, pivotally mounted about a pin 312 at the lower end of the stationary guide frame. Each of the stationary guide frame and the pivotally mounted guide frame has a series of spaced guide elements, each with a central guide aperture therein, which are alternately interleaved, such that the spaced guide elements of the pivotally mounted guide frame alternate with the spaced guide elements of the stationary guide frame. The pivotally mounted guide frame 311 is spring biased about the mounting pin 312 to rotate the top thereof away from the top of the stationary guide frame, such that the suture extending between the alternating stationary guide frame elements and the pivoted guide frame elements is placed under tension while being pulled therethrough.

The suture then extends to and is wrapped twice around a tension roller 314 which is mounted on one end of a torque motor 316, which applies a given tension to the suture as it is pulled through the servo tower by the first and second gripper assemblies 30, 32. Each different suture size and material should have a different tension applied thereto as it is drawn through the apparatus. The torque motor 316 provides a different tension force for each different suture size and type, and the specific tension force (in grams per volt to be applied by the torque motor) is downloaded from a computer program at each suture batch changeover. The proper tension is important for several operations described herein, and is particularly important for the cutter assembly to operate while providing a clean neat cut without a broom effect.

The suture then extends to an out-of-suture sensor positioned at 317, and then through a pair of opposed rollers 318, 320 of a knot detector. One of the pair of rollers is 318 mounted on one end of a lever arm 322, and if a knot travels between the pair of opposed rollers, it pushes the lever arm away, and the movement of the lever arm is detected by a photodetector 324. The suture 55 then travels around an idler roller 320 to change direction, to a further idler roller 328 to change direction again, from which the suture 55 extends vertically downwardly through a heated tipping assembly 330, which heats and ultimately stiffens a small length of the suture, at which the suture is subsequently cut and the cut tip is inserted into and swaged to a needle. The suture 55 then extends downwardly from the tipping assembly to a large idler roller 332 mounted near the bottom of the machine having an appropriately 7 inch diameter, at which the suture reverses direction and travels vertically upwardly to the first and second gripper assemblies 30, 32, only one of which is visible in FIG. 10, the suture cutter assembly 334 and a suture swaging station 336.

Figure 13:
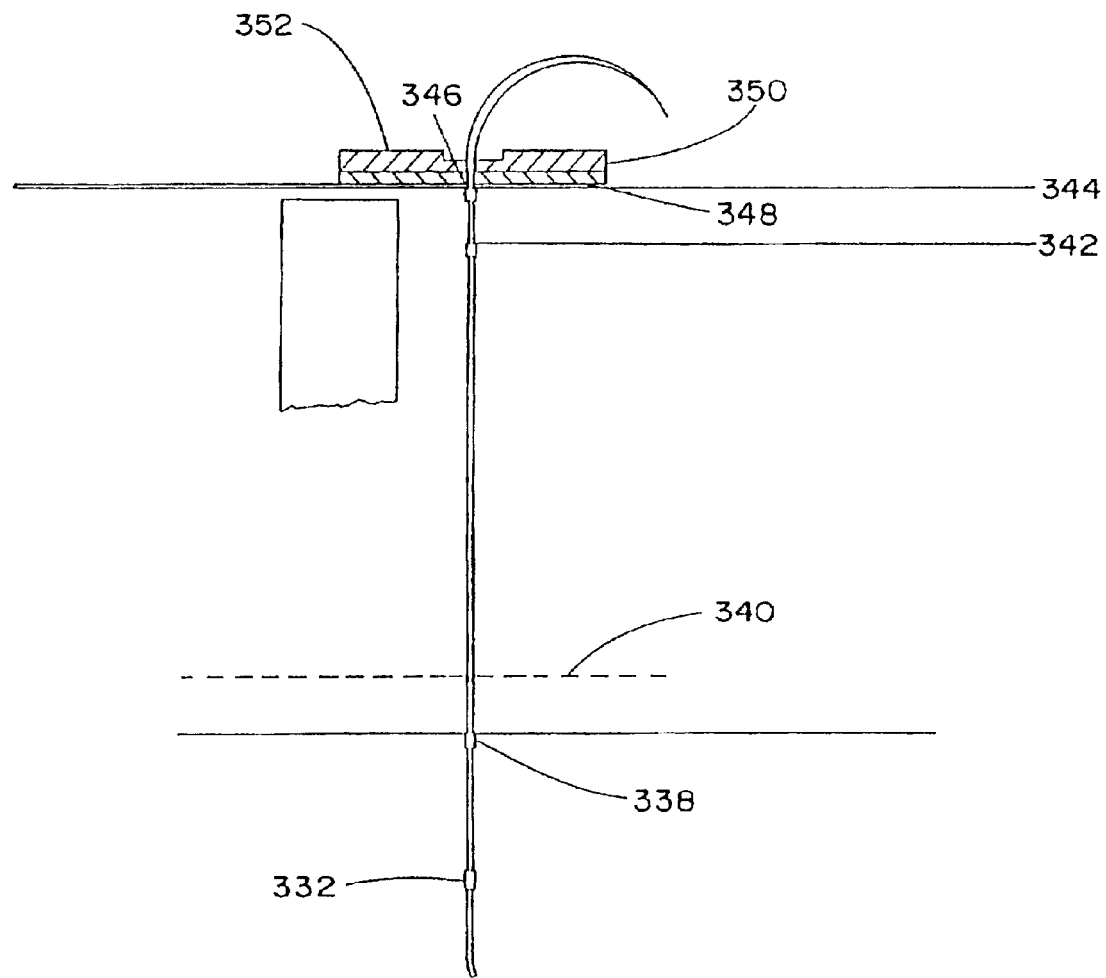
FIG. 13 is a schematic illustration of the different positions in the servo tower including from the bottom, the large idler roller, the bottom servo gripper position, the cut blade position, the home position of the servo gripper, and the final insertion position of the servo gripper.

FIG. 13 is a schematic illustration of the different positions in the servo tower including, from the bottom, the large idler roller 332, the bottom servo gripper position 338, the position 340 of the cutting blade, the home position 342 of the servo gripper, and the final insertion position 344 of the servo gripper. During the insertion operation, the cut suture end is guided by a funnel shaped aperture 346 in a funnel element 348 into the aperture in the end of a needle, after which a moving anvil 350 is moved relative to a stationary anvil 352, of a swage die, to swage and attach the needle to the suture.

In this embodiment, after initialization, one gripper assembly will be in a home position, 2.000" below the face of the swage die mounting surface, allowing a 2.030" movement from the home position to an insert position. A proximity switch is located on each tower at 2.000" below the face of the swage die mounting surface to set the home position during an initialization procedure.

Assuming that the machine is being initially set up to cut a desired length of suture, the cutter assembly 334 will be moved to a predetermined vertical position in the swaging machine by operation of the handcrank 108. This is done by aligning a pointer for the cutter assembly with a vertical scale positioned on the side of the swaging machine at 335, similar to the vertical scale 354 shown in FIGS. 10 and 11 for the tipping assembly.

The cutter assembly includes a proximity switch thereon, and during an initialization procedure, the position of a gripper assembly is detected by the proximity switch, and that position is set in memory to set the servo gripper bottom position 338 during subsequent normal operation of the machine. The tipping assembly is also moved to an appropriate position in the machine as described hereinbelow.

During operation, assume that the lower gripper assembly has just moved up to the home position. At the home position, the gripper assembly stops and waits a predetermined time, during which a needle is preclamped in an insertion position in the swaging station 336, and then moves to the insert position. The following operations are then performed substantially simultaneously. The bottom gripper assembly closes, a tipping operation is performed simultaneously at the tipping assembly 330, and the swage die is simultaneously actuated to swage the needle end around the suture, attaching it thereto. Thereafter, the cutting assembly 334 is activated, cutting in the tipped area to cut the suture to the given length. Thereafter, the upper gripper assembly opens, and the assembly returns to the bottom position, and simultaneously therewith the lower gripper assembly moves up to the home position, and the cycle is then repeated.

After removal of the swaged needle and attached suture length from the apparatus, it is subjected to a sterilization operation, during which the suture length incurs some shrinkage. Accordingly, the cut lengths of suture must be cut to lengths slightly longer than their desired (or label) final lengths to compensate for such shrinkage.

The following table gives, for silk suture, in the left column the commercial (or label) suture length, in the middle column the low servo position of the low gripper assembly below the face of the swage die mounting surface, and in the right column the cut length of suture prior to shrinkage. VICRYL shrinkage during sterilization is approximately 3% of the table values for silk.

| 18" | servo - 16.51 | allowed for 18.380" |
| 27" | servo - 25.51 | allowed for 27.380" |
| 30" | servo - 28.51 | allowed for 30.380" |
| 36" | servo - 34.51 | allowed for 36.380" |

As described above, after heating of a predetermined length of suture at the tipping assembly, the suture must cool to allow setting and hardening of the suture material prior to cutting of the suture at the hardened length and insertion of the cut stiffened end into a needle. This cooling of the suture is provided in this embodiment by allowing a discrete number of machine cutting cycles to occur between tipping of the suture and cutting of the suture. This is provided by allowing a predetermined long length of suture travel between the tipping assembly and the cutter assembly. Hence, the suture tipping assembly 330 is positioned near the top of the servo tower, and after heating thereat, the suture travels to the bottom of the machine, around the large idler roller 332 thereat, and then back upwardly to the cutter assembly 334. The large diameter of the idler roller 332, relative to the other idler roller 320, 328, is provided because the small length of suture which has been heated at the tipping assembly 330, has begun to harden and set by the time the heated section reaches the large idler roller. The large diameter thereof facilitates the suture to travel therearound without picking up a permanent curved set from the large idler roller, as it is desirable for the suture to be straight, without any curve, when it is subsequently cut and inserted into a needle. The idler rollers 320 and 328 typically have a 0.5 inch diameter, whereas the large diameter roller 332 has a diameter preferably greater than 6.0 inches, approximately 7.0 inches in one embodiment.

The operation of the machine depends upon a discrete whole number of machine cutting operations to be performed between the tipping and cutting operations. Accordingly, for each different length of cut suture, the tipping assembly 330 must be positioned at a different predetermined position within the machine for the tipped section of suture to be precisely and correctly positioned at the cutter assembly 334 after a given number of machine cycles.

The following table gives in its columns, proceeding from left to right, the label suture length, the actual cut suture length, the number of machine cycles or increments provided between tipping and cutting, the total travel length of the suture between tipping and cutting, the tipping assembly vertical position above the table top, and the tipping assembly scale pointer position above the table top (explained in greater detail hereinbelow).

| SUTURE LENGTH | | INCREMENTS | TOTAL | ABOVE TABLE TOP | |
| --- | --- | --- | --- | --- | --- |
| LABEL | ACTUAL | | | TIPPER C | POINTER |
| 18 IN. | 19 IN. | 6 | 114 IN. | 27.64 IN. | 25.89 IN. |
| 27 IN. | 28 IN. | 4 | 112 IN. | 25.64 IN. | 23.89 IN. |
| 30 IN. | 31 IN. | 4 | 124 IN. | 37.64 IN. | 35.89 IN. |
| 36 IN. | 36.25 IN. | 3 | 108.75 IN. | 22.39 IN. | 20.64 IN. |

Figure 11:
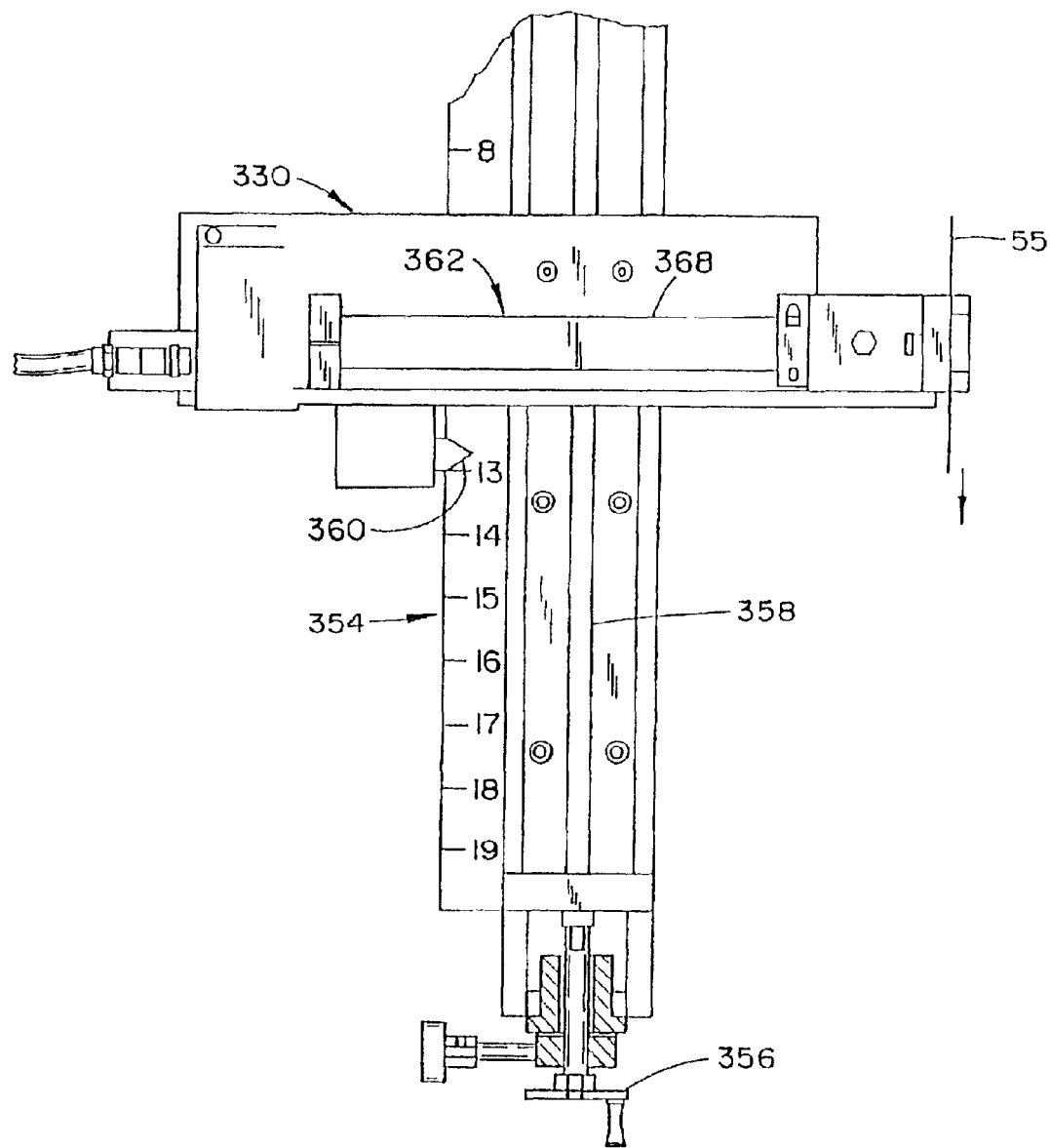
FIG. 11 illustrates an enlarged front elevational view of the suture tipping assembly at which a small length of the suture is heated to stiffen the suture material after subsequent cooling thereof, and also illustrates the adjustable movement thereof along a vertical scale provided adjacent to the tipping assembly.

FIG. 11 illustrates an enlarged front elevational view of the suture tipping assembly at which a small length of the suture is heated to stiffen the suture material after subsequent cooling thereof, in preparation for cutting a given length of the suture and inserting the lead cut end of the suture into the end of a needle for swaging thereto. FIG. 11 illustrates the movement of the tipping assembly 330 along a vertical scale 354 provided adjacent to the tipping assembly 330. The vertical position of the tipping assembly in the machine is adjustable by a handcrank 356 and precision leadscrew 358, similar to the positioning mechanism for the cutter assembly as described hereinabove. As the handcrank is rotated, the vertical position of the tipping assembly 330 in the machine is changed, and is precisely positioned by reading a pointer 360 attached to the tipping assembly on the scale 354. A chart is provided for the machine which gives, for each desired length of suture, the appropriate position for pointer 360 of the tipper assembly 330 on the vertical scale 354, and a similar position for the cutter mechanism 334 on the vertical scale 335.

In this embodiment, the position of the cutting mechanism along the drawing axis is continuously adjustable to provide an infinite number of possible different lengths of cut suture. For each different cutting position of the cutting mechanism, the tipping mechanism is adjustably positioned at a different, predetermined position in the apparatus to provide for the tipped section of suture to be precisely positioned at the cutter mechanism after a discrete number of machine cycles.

In an alternative embodiment which does not have this infinite adjustment feature, several standard lengths of suture are accommodated by several standard positions which are fixed in the machine by pins which secure the cutter mechanism to the machine frame by pin receiving holes in the machine at the standard positions. For example, the cutter mechanism might be moved to a position for cutting 18" sutures and be secured to the frame by the placement pins being inserted into the pin receiving holes in the machine for 18" sutures. The cutter mechanism might also be moved to positions for cutting 27", 30", or 36" sutures by moving the placement pins to the pin receiving holes in the machine provided for those length sutures. Each different position can have a separate proximity switch provided therefor, which indicates the cutting mechanism position to the controller, which then downloads the appropriate servo gripper bottom position. The appropriate tipping mechanism position is known for each different cutter mechanism position.

Figure 12:
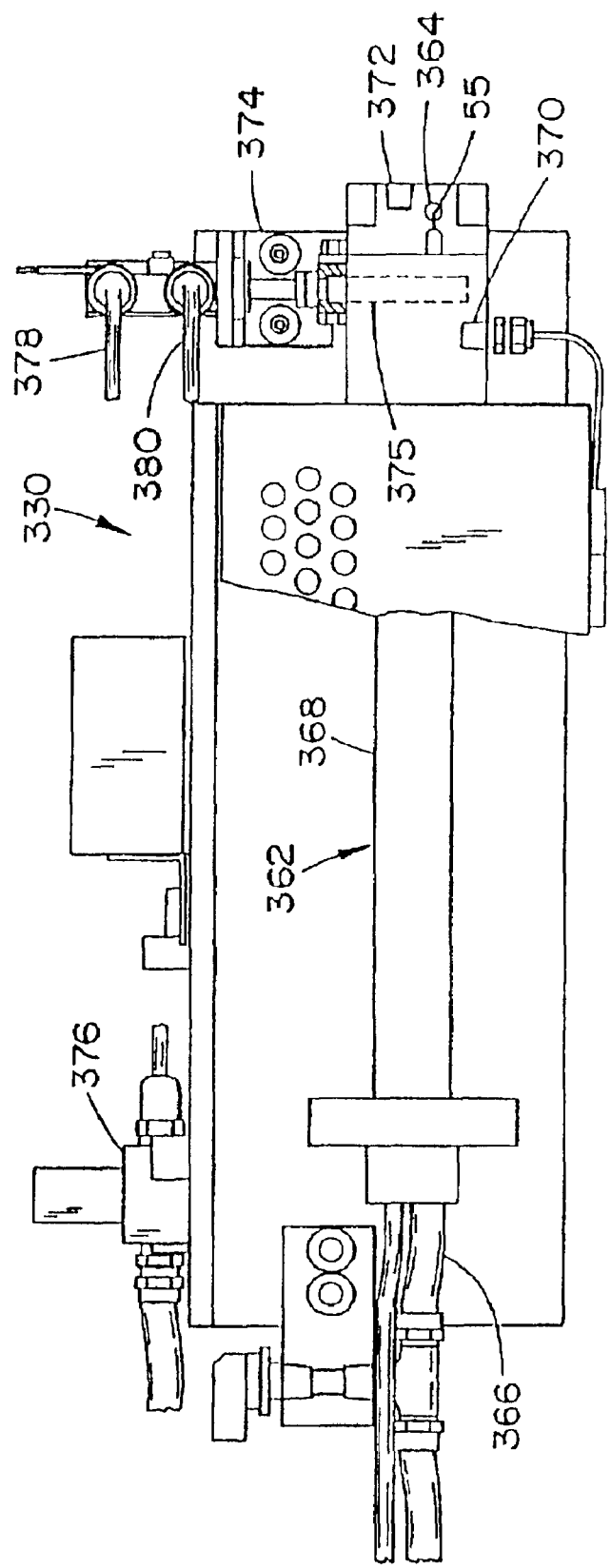
FIG. 12 is an enlarged top plan view of the tipping assembly shown in FIGS. 10 and 11, and illustrates further details of the flow of heated air through the tipping assembly and its control to selectively heat and tip a small length of the suture.

FIGS. 11 and 12 illustrate the heater 362 in the tipping assembly 330 and the vertical movement of the suture 55 down (front view, FIG. 11) and through (top view, FIG. 12) a suture tipping aperture 364, FIG. 12, positioned on the right side of the tipping assembly. FIG. 12 illustrates further details of the flow of heated air through the tipping assembly and its control to selectively heat and tip the suture. As described previously, the tipping assembly 330 is mounted near the top of the machine so that it takes a discrete number of machine cycles for the suture to reach the cut position. This gives the tipped area time to cool down before the cutting and insertion operations. The tipping assembly operates by flowing air supplied at a regulated pressure through an inlet air duct 366 at a regulated flow rate, in one embodiment 195 CFH (Cubic Feet per Hour), over a heater coil mounted within an outer heater casing 368. Air is supplied to a flowmeter at a regulated pressure required to maintain 195 CFH of air flowing over the heater coil. A thermocouple 370 is positioned in the air flow at the discharge end of the heater casing 368, to monitor and control the air temperature through a controller in a programmable logic controller (PLC). The tipping assembly 330 is operated at various temperatures between 200° F. and 550° F. depending upon the particular suture material to be run. The particular temperature is a down loaded parameter from an operating program at each suture batch changeover. The tipping assembly guides the suture and provides a 2.000" long heating aperture 364 for the tipping length.

The constant flow of heated air at the outlet of the heater casing 368 flows either 1) through the heating aperture 364 in which the suture 55 is intermittently stopped and positioned during a tipping operation, or 2) alternatively the heated air is dumped into the surrounding atmosphere through a diverter channel 372, FIG. 12. The flow of hot air is controlled by an air cylinder 374, under control of a solenoid 376, which controls the flow of actuating air through air tubes 378, 380. The air cylinder 374 controls the position of a retractable slide element having a flow aperture therein which is selectively positioned in front of either 1) a channel into the heating aperture 364 or 2) the diverter channel 372, depending upon the position of the slider element which is controlled by an air cylinder.

As an example, the following control parameters have been established for heat tipping of Braided VICRYL sutures sizes 1, 0, 2/0, 3/0 and 4/0. The suture tension refers to the tension force in grams which the tension roller 314 and torque motor 316 apply to the suture as it is being drawn through the machine by the grippers.

| Suture Size | Tipping Temp. +/−25 deg. | Tipping Time +/−25 Ms | Suture Tension +/−25 Grams |
|---|---|---|---|
| 4/0 | 375 F. | 380 | 275 |
| 3/0 | 395 F. | 380 | 275 |
| 2/0 | 410 F. | 380 | 275 |
| 0 | 425 F. | 380 | 275 |
| 1 | 435 F. | 380 | 275 |

As a further example, the following control parameters have been established for suture tension and heat tipping of silk sutures sizes 2/0, 3/0 and 4/0. In the following table the left column lists commercial needle types, the next column needle sizes, the next column suture sizes, the next column suture tension in grams applied by the tension roller 314, the next column tipping dwell time, the next column tipping heated air flow in standard cubic feet per minute, and the right column suture tipping temperature.

SILK SUTURE AND TIPPING PARAMETERS

| Needle type Tolerance | Wire Size (0.000") N/A | Suture Size N/A | Suture Tension (grams) (±10 grams) | Tipping Dwell (seconds) (±0.020) | Tipping Air Flow (SCFM) (±5) | Tipping Temperature (° F.) (±15) |
|---|---|---|---|---|---|---|
| CT-1 | 39 | 2–0 | 275 | 0.380 | 190 | 300 |
| CT-2 | 39 | 2–0 | 275 | 0.380 | 190 | 300 |
| SH | 26 | 2–0 | 275 | 0.380 | 190 | 300 |
| SH | 24 | 3–0 | 275 | 0.380 | 190 | 300 |
| SH | 22 | 4–0 | 275 | 0.380 | 190 | 300 |
| SH-1 | 22 | 3–0 | 275 | 0.380 | 190 | 300 |
| SH-1 | 18 | 4–0 | 275 | 0.380 | 190 | 300 |

The previous tables are for braided VICRYL suture and silk suture, and similar tables could be developed for other suture materials such as Ethibond (braided polyester) and monofilament and braided nylon.

Figure 14:
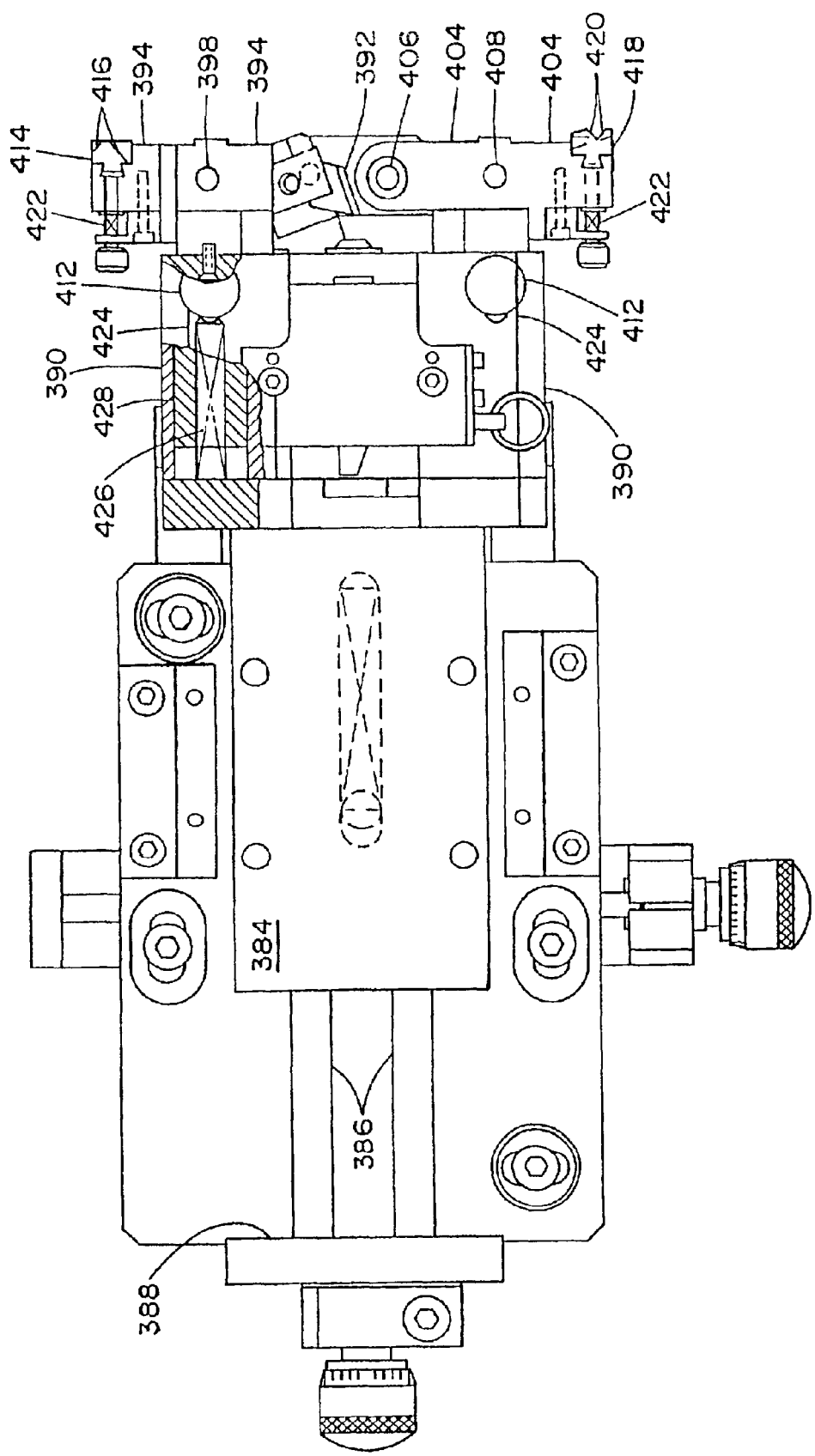
FIG. 14 illustrates a top plan view of a cutter assembly pursuant to the present invention, shown in a retracted position.
Figure 15:
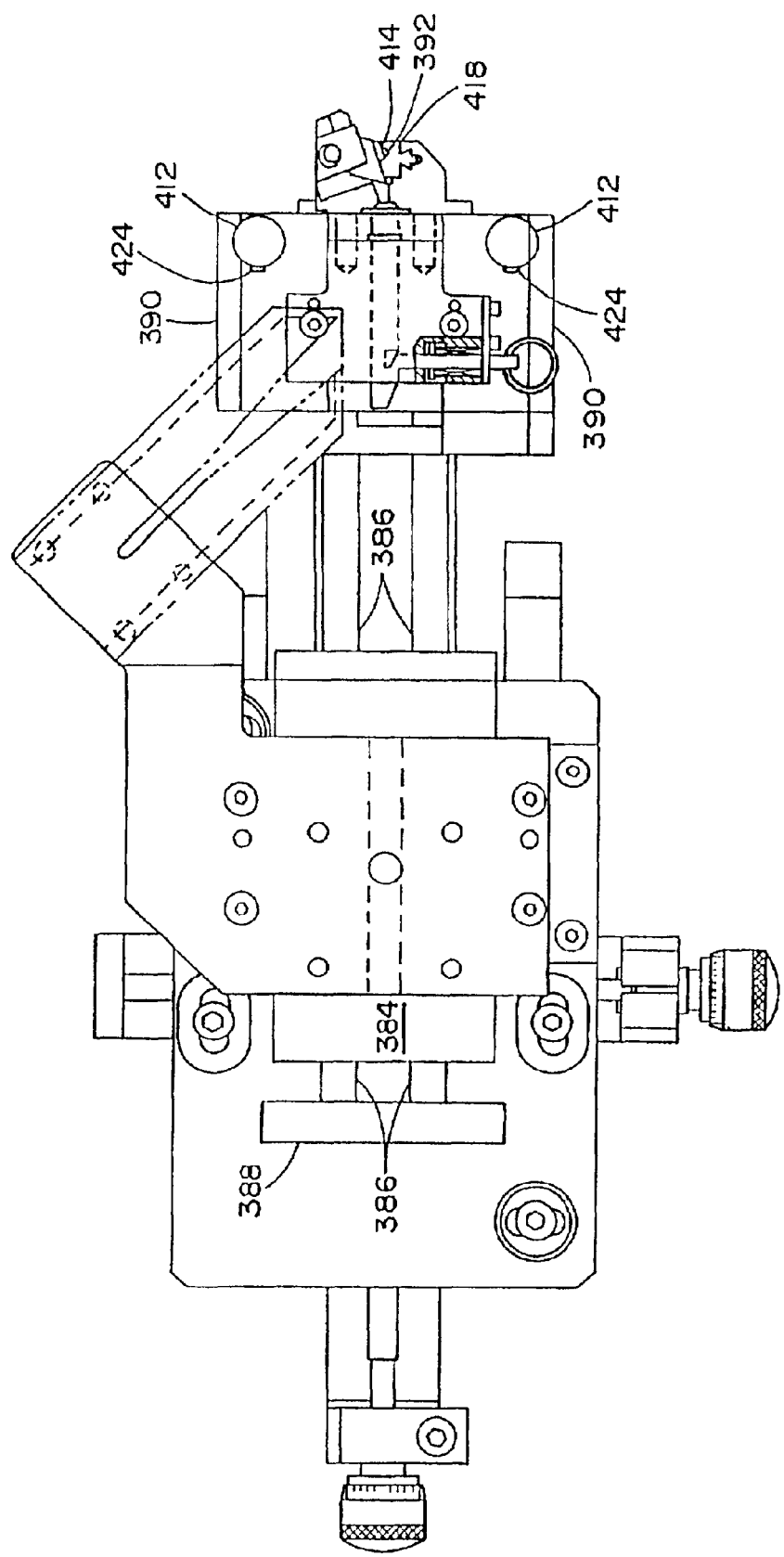
FIG. 15 is a top plan view of the cutter assembly of FIG. 14, shown in an extended cutting position.
Figure 16:
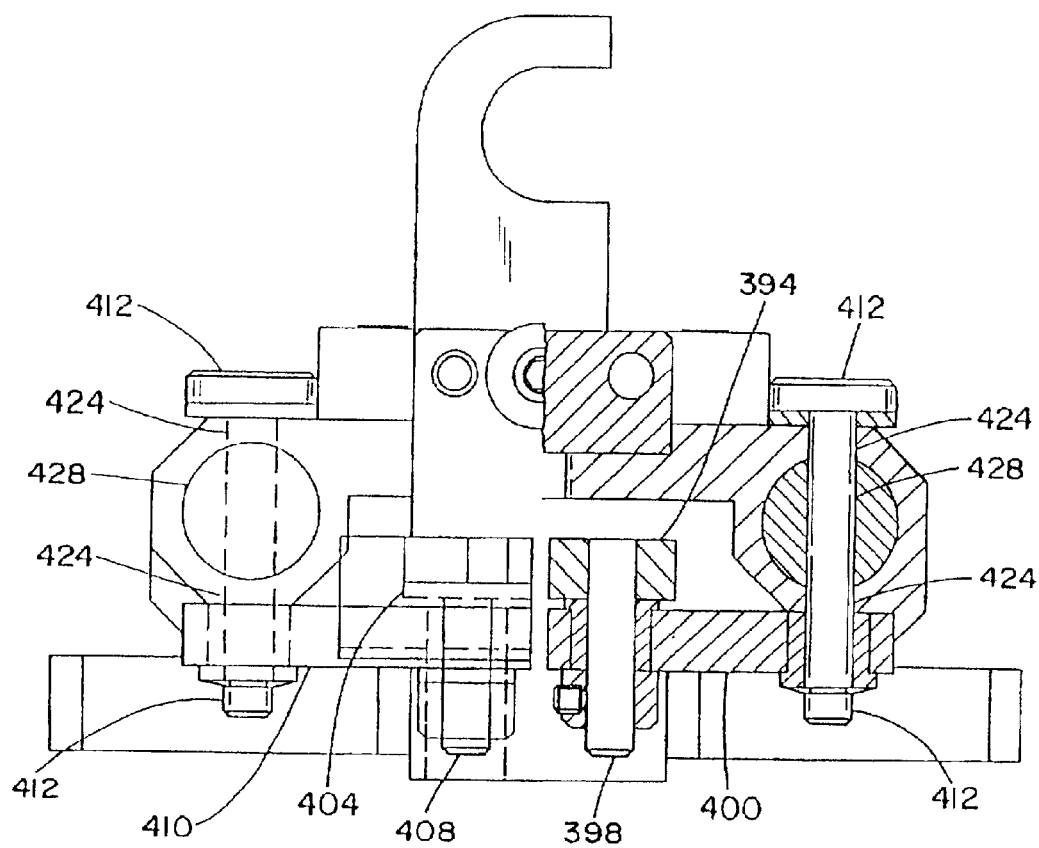
FIG. 16 is a front elevational view of the cutter assembly of FIGS. 14 and 15, and illustrates further details of the drive mechanisms for the cutter assembly.

FIG. 14 illustrates a top plan view of a cutter assembly pursuant to the present invention, shown in a retracted position. FIG. 15 is a top plan view of the cutter assembly of FIG. 14, shown in an extended cutting position. FIG. 16 is a front elevational view, similar to that of FIG. 10, partly in section, of the cutter assembly 334 of FIGS. 14 and 15, and illustrates further details of the drive mechanisms for the cutter assembly.

The cutter assembly is actuated by an air cylinder 384 which during a cutting operation drives a slide mechanism (blade overtravel block) 390 from the retracted position of FIG. 14 to the extended position of FIG. 15. The air cylinder 384 mounts two drive rods 386 which extend therethrough and which the air cylinder translates back and forth to extend and retract the cutter assembly. A transverse bar 388 connects the two drive rods 386 at their ends remote from the cutter mechanism. The other ends of the two drive rods 386 are connected to the slide mechanism (blade overtravel block) 390, on which the knife blade 392 is mounted by a suitable mounting structure for movement therewith.

Referring to FIGS. 14, 15 and 16, a first locator arm 394 is pivoted about a first stationary pin (not visible in FIG. 14 but similar to 406) at its inner end, and is pivotally mounted by a drive pin 398 to a first link arm 400 near its middle portion. Likewise, a second opposed locator arm 404 is pivoted about a second stationary pin 406 at its inner end, and is pivotally mounted by a drive pin 408 to a second link arm 410 near its middle portion. The second ends of the first and second link arms 400, 410 are secured to overtravel pins 412 which are mounted to the blade overtravel block 390, as illustrated in FIG. 16.

During operation, as the blade overtravel block 390 is driven by the air cylinder 384 to the extended position, the first and second link arms 400, 410 are pulled by the overtravel pins 412, which in turn pull the drive pins 398, 408 of the first and second locator arms 394, 404. This causes the first and second locator arms 394, 404 to rotate from the open position of FIG. 14 to the closed position of FIG. 15, and causes the first and second link arms to rotate to the position shown in FIGS. 15 and 16. The first locator arm 394 has a first insert 414 removably positioned at its end having a convex V shape 416, and the second locator arm 404 has a second insert 418 removably positioned at its end having a concave V shape 420. When the first and second link arms are rotated together as shown in FIG. 15, the convex V insert 414 clamps against the concave V insert 418 to secure the suture therebetween at the points of the Vs. The inserts are removable, and also secured in place, by set screws 422 in the link arms.

The overtravel pins 412 are not mounted fixedly to the overtravel block 386, but are mounted in elongated slots 424 in the overtravel block 390, and are mounted against spring-loaded pistons 428, which are biased by springs 426. After the locator arms 394, 404 clamp against each other, further movement of the overtravel block 390 causes the overtravel pins 412 to compress the spring-loaded pistons 428 and translate in their slots 424.

During a cutting operation, as the air cylinder 384 drives the blade overtravel block 390 to the right from the retracted position of FIG. 14 to the extended position of FIG. 15, the first link arm 400 and locator arm 394 are driven in clockwise rotations as viewed in FIGS. 14 and 15, and the second link arm 410 and locator arm 404 are driven in counter-clockwise rotations as viewed in FIGS. 14 and 15. They are driven until the convex V insert 414 positioned at the distant end of the first locator arm 394 is seated into the concave V insert 418 positioned at the end of the second locator arm 404 to assume the position of FIG. 15, with the suture positioned and clamped between the points of the Vs of the inserts. The knife blade 392 is mounted on and is also driven to the right by the blade overtravel block 390 to assume the position shown in FIG. 15. Further movement to the right by the blade overtravel block 390 causes a compression of the springs 426 positioned behind the pistons 428, such that the inserts 414, 418 and clamped suture are now stationary. However, further movement to the right by the blade overtravel block causes the knife blade 392 to continue to translate to the right relative to the then-stationary positioning inserts 414, 418 and to sever the suture held therebetween. The cutting blade 392 translates along the side surfaces of the inserts, as best illustrated in FIG. 17, and cuts the suture.

Figure 17:
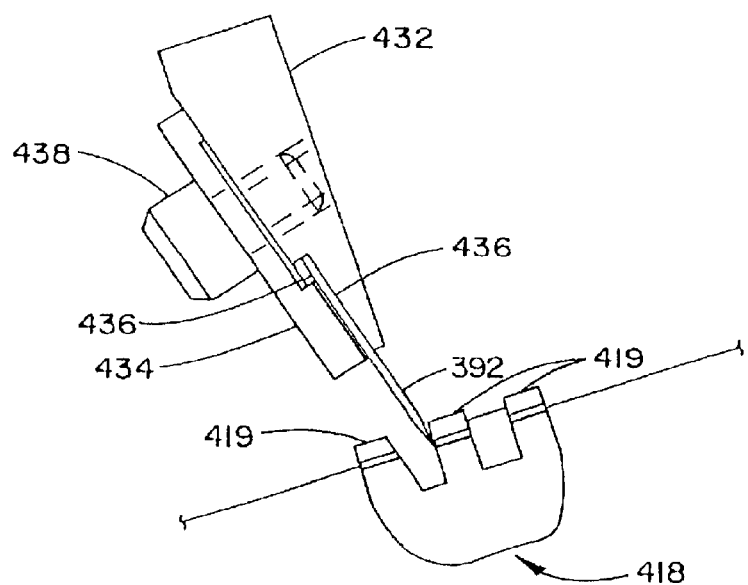
FIG. 17 is an enlarged end view of the knife blade in its mounting positioned relative to one edge of the concave V insert and also illustrates further details of the concave V insert.

FIG. 17 illustrates a side profile of the concave V 418 insert which has three separate concave V arms 419 to position the suture. The convex V insert has three similar separate convex V arms, and the knife blade slides adjacent to the center V arms, as shown in FIG. 17, to cut the suture. FIG. 17 also illustrates the knife blade 392 which is seated in a positioning slot 436 between a blade mounting structure 432 and a removable blade cap 434 which is secured to the blade mounting structure 432 by a removable screw 438.

While the invention has been particularly shown and described with respect to preferred embodiments thereof, it will be understood by those skilled in the art that the foregoing and other changes in form and details may be made therein without departing from the spirit and scope of the invention, which should be limited only by the scope of the appended claims.

What is claimed:

1. A method for cutting an indefinite length of suture to uniform lengths for subsequent threading and swaging to surgical needles having a suture receiving opening formed therein, comprising:

(a) feeding the indefinite length suture to a drawing axis of an apparatus for drawing and cutting thereof, said drawing axis being defined as being parallel to first and second longitudinal members of a drawing frame of said apparatus;

(b) heating a predetermined small length of the suture to stiffen the small length of suture after subsequent cooling thereof, in preparation for cutting the suture at the stiffened small length and inserting a stiffened lead cut end of the suture into an end of a needle for swaging thereto;

(c) gripping said indefinite length suture and alternately drawing it along said drawing axis by first and second gripping means, said first and second gripping means being mounted for reciprocal movement on at least one of said first and second longitudinal members, wherein one of said first and second gripping means draws the indefinite length suture to a position beyond said cutting means, while the other of said first and second gripping means reciprocates to a start position along said drawing axis before said cutting means, such that the first and second gripping means are used alternately to draw said indefinite length suture through the apparatus and to feed said indefinite length suture into a needle;

(d) cutting said indefinite length suture to provide uniform lengths of suture;

(e) providing a predetermined long length of suture travel between the heating step and the cutting step, which is a discrete number, two or more, times the uniform length of suture being cut by the apparatus, to provide a discrete number, two or more, of apparatus cutting cycles between heating of the suture and cutting of the suture, whereby after heating of a small length of suture, the suture is cooled to allow setting and hardening of the suture material prior to cuffing.

2. A method as claimed in claim 1, wherein said discrete number comprises at least three.

3. A method as claimed in claim 2, including guiding the suture to the heating step by at least one small diameter idler roller, and after heating thereat, drawing the suture around a large diameter idler roller, large relative to the diameter of the small diameter idler roller, which is provided because the small length of suture which has been heated has begun to harden and set by the time the heated suture reaches the large diameter idler roller, and the large diameter thereof facilitates the suture to travel therearound and change direction without picking up a permanent curve set from the large idler roller, to provide a straight suture, without any curve, when it is subsequently cut and inserted into a needle.

4. A method as claimed in claim 3, including heating the suture near the top of the apparatus, and positioning the large diameter idler roller near the bottom of the apparatus, such that the suture reverses direction at the large diameter roller and is drawn vertically upwardly to the first and second gripping means.

5. A method as claimed in claim 4, including providing the large idler roller with a diameter larger than 6 inches.

6. A method as claimed in claim 1, including guiding the suture to the heating step by at least one small diameter idler roller, and after heating thereat, drawing the suture around a large diameter idler roller, large relative to the diameter of the small diameter idler roller, which is provided because the small, length of suture which has been heated has begun to harden and set by the time the heated suture reaches the large diameter idler roller, and the large diameter thereof facilitates the suture to travel therearound and change direction without picking up a permanent curve set from the large idler roller, to provide a straight suture, without any curve, when it is subsequently cut and inserted into a needle.

7. A method as claimed in claim 6, including heating the suture near the top of the apparatus, and positioning the large diameter idler roller near the bottom of the apparatus, such that the suture reverses direction at the large diameter roller and is drawn vertically upwardly to the first and second gripping means.

8. A method as claimed in claim 6, including providing the large diameter idler roller with a diameter larger than 6 inches.

9. A method as claimed in claim 8, including providing the large diameter idler roller with a diameter of substantially 7 inches.

10. A method as claimed in claim 1, including performing the cutting at any position along the drawing axis to provide an infinite number of possible different lengths of cut suture.

11. A method as claimed in claim 10, wherein for each different position of the cutting step, the heating is performed at a different predetermined position to precisely position the stiffened small length of suture at a cutter means after said discrete number of apparatus cycles for cuffing said indefinite length suture.

12. A method as claimed in claim 11, including positioning the suture for heating by positioning a pointer adjacent to a specified reading on a linear measurement scale stationarily positioned in the apparatus.

13. A method as claimed in claim 12, including positioning the suture for heating in the apparatus by rotating a handcrank and precision leadscrew.

14. A method as claimed in claim 10, including positioning the suture for heating by positioning a pointer adjacent to a specified reading in a linear measurement scale stationarily positioned in the apparatus.

15. A method as claimed in claim 10, including positioning the suture for heating in the apparatus by rotating a handcrank and precision leadscrew.

16. A method as claimed in claim 1, including applying a given tension to the suture as it is pulled through the apparatus by the first and second gripping means by wrapping the suture around a tension roller which is mounted on one end of a torque motor.

17. A method as claimed in claim 16, including wrapping the suture around the tension roller a multiple number of times.

18. A method as claimed in claim 17, including wrapping the suture around the tension roller twice.

19. A method as claimed in claim 1, including positioning a releasable suture clamp on each of the first and second gripping means, and clamping the suture with the releasable suture clamp during an initial auto threading of a new lead of suture through the apparatus.

* * * * *